US008592806B2

(12) United States Patent
Qu et al.

(10) Patent No.: US 8,592,806 B2
(45) Date of Patent: Nov. 26, 2013

(54) QUINONE COMPOUNDS AS DOPANTS IN ORGANIC ELECTRONICS

(75) Inventors: Jianqiang Qu, Shanghai (CN); Nicolle Langer, Heppenheim (DE); Ingmar Bruder, Harthausen (DE); Imke Britta Mueller, Heidelberg (DE); Soichi Watanabe, Mannheim (DE)

(73) Assignee: Novaled AG, Dresden (DE)

( * ) Notice: Subject to any disclaimer, the term of this patent is extended or adjusted under 35 U.S.C. 154(b) by 204 days.

(21) Appl. No.: 13/203,299

(22) PCT Filed: Feb. 25, 2010

(86) PCT No.: PCT/EP2010/052400
§ 371 (c)(1),
(2), (4) Date: Nov. 7, 2011

(87) PCT Pub. No.: WO2010/097433
PCT Pub. Date: Sep. 2, 2010

(65) Prior Publication Data
US 2012/0217483 A1 Aug. 30, 2012

(30) Foreign Application Priority Data
Feb. 26, 2009 (EP) .................................... 09153776

(51) Int. Cl.
H01L 35/24 (2006.01)
(52) U.S. Cl.
USPC ..................................... 257/40; 257/E51.001
(58) Field of Classification Search
USPC ........................................... 257/40, E51.001
See application file for complete search history.

(56) References Cited

U.S. PATENT DOCUMENTS

| 4,461,922 | A | 7/1984 | Gay et al. |
|---|---|---|---|
| 6,198,091 | B1 | 3/2001 | Forrest et al. |
| 6,198,092 | B1 | 3/2001 | Bulovic et al. |
| 6,451,415 | B1 | 9/2002 | Forrest et al. |
| 6,864,396 | B2 | 3/2005 | Smith et al. |
| 6,908,783 | B1 | 6/2005 | Kuehl et al. |
| 7,084,273 | B2 | 8/2006 | Stoessel et al. |
| 7,846,763 | B2 | 12/2010 | Bold et al. |
| 2001/0015432 | A1 | 8/2001 | Igarashi |
| 2001/0019782 | A1 | 9/2001 | Igarashi et al. |
| 2002/0024293 | A1 | 2/2002 | Igarashi et al. |
| 2002/0048689 | A1 | 4/2002 | Igarashi et al. |
| 2002/0055014 | A1 | 5/2002 | Okada et al. |
| 2002/0094453 | A1 | 7/2002 | Takiguchi et al. |
| 2003/0100779 | A1 | 5/2003 | Vogel et al. |
| 2004/0046182 | A1 | 3/2004 | Chen et al. |
| 2005/0227406 | A1 | 10/2005 | Shtein et al. |

(Continued)

FOREIGN PATENT DOCUMENTS

| EP | 1191612 A2 | 3/2002 |
|---|---|---|
| EP | 1191613 A2 | 3/2002 |

(Continued)

OTHER PUBLICATIONS

Brabec et al., 2001, "Plastic Solar Cells," Adv. Funct. Mater., 11(1):15-26.

(Continued)

Primary Examiner — Anthony Ho
(74) Attorney, Agent, or Firm — Sutherland Asbill & Brennan LLP

(57) ABSTRACT

The invention relates to novel quinone compounds and to the use thereof as dopants in organic electronics.

22 Claims, 1 Drawing Sheet

(56) References Cited

U.S. PATENT DOCUMENTS

| | | |
|---|---|---|
| 2006/0202195 A1 | 9/2006 | Marks et al. |
| 2007/0190783 A1 | 8/2007 | Gomez et al. |
| 2008/0018221 A1 | 1/2008 | Egen et al. |
| 2009/0054657 A1 | 2/2009 | Molt et al. |
| 2009/0096367 A1 | 4/2009 | Fuchs et al. |
| 2009/0278119 A1 | 11/2009 | Schildknecht et al. |
| 2010/0219403 A1 | 9/2010 | Langer et al. |
| 2011/0031477 A1 | 2/2011 | Langer et al. |
| 2011/0034699 A1 | 2/2011 | Fuchs et al. |

FOREIGN PATENT DOCUMENTS

| | | |
|---|---|---|
| EP | 1211257 A2 | 6/2002 |
| WO | 00/70655 A2 | 11/2000 |
| WO | 01/41512 A1 | 6/2001 |
| WO | 02/02714 A2 | 1/2002 |
| WO | 02/15645 A1 | 2/2002 |
| WO | 2005/1113704 A2 | 12/2005 |
| WO | 2006/067074 A1 | 6/2006 |
| WO | 2006/100298 A1 | 9/2006 |
| WO | 2006/115301 A1 | 11/2006 |
| WO | 2006/121811 A1 | 11/2006 |
| WO | 2007/095118 A2 | 8/2007 |

OTHER PUBLICATIONS

Drechsel et al., 2004, "High Efficiency Organic Solar Cells Based on Single or Multiple PIN Structures," Thin Solid Films 451-452:515-517.

Drechsel et al., 2004, "MIP-type Organic Solar Cells Incorporating Phthalocyanine/Fullerene Mixed Layers and Doped Wide-Gap Transport Layers," Organic Electronics, 5:175-186.

Facchetti et al., 2005, "Gate Dielectrics for Organic Field-Effect Transistors: New Opportunities for Organic Electronics," Adv. Mater, 17:1705-1725.

Gao et al., 2003, "Controlled p Doping of the Hole-Transport Molecular Material N,N'-diphenyl-N,N'-bis(1-naphthyl)-1,1'-biphenyl-4,4'-diamine with Tetrafluorotetracyanoquinodimethane," Journal of Applied Physics, 94 (1):359-366.

Gustafsson et al., 1992, "Flexible Light-Emitting Diodes Made from Soluble Conducting Polymers," Nature, 357:477-479.

Karl et al., 1994, "Efficient Organic Photovoltaic Cells," Mol. Cryst. Liq. Cryst., 252:243-258.

Kirk-Olthmer Encylopedia of Chemical Technologies, 4(18):837-860, 1996.

Maenning et al., 2004, "Organic p-i-n Solar Cells," Appl. Phys. A 79:1-14.

Muehlbacher et al., 2006, "High Photovoltaic Performance of a Low-Bandgap Polymer," Adv. Mater, 18:2884-2889.

Peumans et al., 2003, "Small Molecular Weight Organic Thin-Film Photodetectors and Solar Cells," Journal of Applied Physics, 93(7):3693-3723.

Pfeiffer et al., 2003, "Doped Organic Semiconductors: Physics and Application in Light Emitting Diodes," Organic Electronics, 4:89-103.

Tang, 1986, "Two-Layer Organic Photovoltaic Cell," Appl. Phys. Lett., 48(2):183-185.

Werner et al., 2003, "Pyronin B as a Donor for n-Type Doping of Organic Thin Films," Applied Physics Letters, vol. 82(25):4495-4497.

QUINONE COMPOUNDS AS DOPANTS IN ORGANIC ELECTRONICS

CROSS-REFERENCE TO RELATED APPLICATIONS

This is a submission pursuant to 35 U.S.C. 154(d)(4) to enter the national stage under 35 U.S.C. 371 for PCT/EP2010/052400, filed Feb. 25, 2010. Priority is claimed under 35 U.S.C. 119(a) and 35 U.S.C. 365(b) to European Patent Application Number 09 153776.1, filed Feb. 26, 2009.

FIELD OF THE INVENTION

The present invention relates to new quinone compounds and to the use thereof as dopants in organic electronics.

BACKGROUND OF THE INVENTION

It is expected that organic semiconductors based on low-molecular or polymer materials will also be used increasingly in the future in many fields of the electronics industry alongside conventional inorganic semiconductors. These materials afford many advantages compared to conventional inorganic semiconductors, for example an improved substrate compatibility and an improved processability of the semiconductor components based thereon. They allow processing on flexible substrates and make it possible to adapt their frontier orbital energies to the respective field of application using the methods of molecular modelling. "Organic electronics" focuses on the development of new materials and manufacturing processes for the production of electronic components based on organic semiconductor layers. Above all, these include organic light-emitting diodes (OLEDs), organic field-effect transistors (OFETs) and organic photovoltaics. A high development potential, for example in storage cells and integrated optoelectronic devices, is attributed to organic field-effect transistors. In organic light-emitting diodes (OLEDs) the property of materials is utilised to emit light when these materials are excited by electric current. In particular, OLEDs are an interesting alternative to cathode ray tubes and liquid crystal displays for the production of flat screens. Owing to the very compact construction and the intrinsically relatively low power consumption, devices which contain OLEDs are suitable in particular for mobile applications, for example for applications in mobile telephones, laptops, etc. A high development potential is also attributed to materials which have maximum transport distances and high mobilities for light-induced excited states (high exciton diffusion lengths) and are therefore advantageously adapted for use as an active material in organic solar cells, particularly in "excitonic solar cells".

It is known to modify the electronic properties of silicon semiconductors by doping. An increase in conductivity is achieved by generation of charge carriers and, depending on the type of doping agent (dopants) used, the Fermi level of the semiconductor is modified.

It is further known that the electrical conductivity of organic semiconductors can also be influenced by doping. Organic semiconducting materials can be formed from compounds having good electron donor properties or good electron acceptor properties. Strong electron acceptors such as tetracyano quinone dimethane (TCNQ) or 2,3,5,6-tetrafluorotetracyano-1,4-benzene quinone methane (F4TCNQ) are known for doping electron donor materials. These produce "holes" in electron-donor-like base materials (hole transport materials) by electron transfer processes, the number and mobility of these holes changing the conductivity of the base material. For example, N,N'-perarylated benzidines, N'N', N"-perarylated starburst compounds or specific metal phthalocyanines, such as zinc phthalocyanine (ZnPc) in particular, are known as materials having hole transport properties.

EP 1 596 445 A1 describes the use of quinine derivatives, which exhibit a lower volatility than tetrafluorotetracyano quinone dimethane (F4TCNQ) under identical evaporation conditions, for doping an organic semiconductor matrix material. In practice 1,4-quinone diimines substituted with fluorine and/or chlorine as well as 1,4,5,8-tetrahydro-1,4,5,8-tetrathia-2,3,6,7-tetracyano anthraquinone (CN4TTAQ) are used. Their tendency to migrate into adjacent undoped layers is a drawback, particularly with halogen-containing dopants. In addition, the service life of electronic components produced therefrom, and in particular of OLEDs could also be improved.

There is also a great need for new dopants for organic electronics having advantageous electronic and application-specific properties.

BRIEF SUMMARY

It has now surprisingly been found that quinone derivatives which contain a combination of cyano groups and phthalimide groups are characterised by their easy accessibility and very good properties for a use as dopants in organic electronics. In particular, these are also halogen-free dopants. They are characterised in particular by a high thermostability and/or can sublimate at high temperatures. Compared to known dopants, an undesired migration into adjacent undoped layers can preferably be avoided or largely reduced with use in electronic components. Compared to known dopants, electronic components based on the quinone derivatives according to the invention are generally characterised by a considerably longer service life.

A first subject matter of the invention is a quinone derivative of general formula (I)

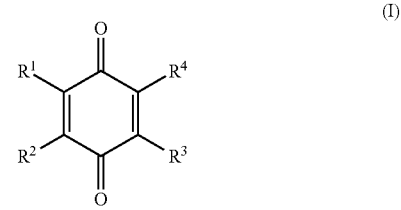

wherein 1, 2 or 3 of the radicals R1 to R4 stand for CN, 1, 2, or 3 of the radicals R1 to R4, independently of one another, stand for a phthalimide radical of general formula (II)

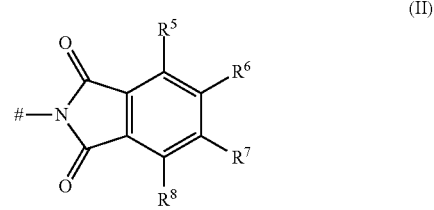

wherein # stands for the linking point to a ring carbon atom of the quinone ring, R5, R6, R7 and R8, independently of one another, stand for hydrogen, fluorine, chlorine, bromine, cyano, nitro, nitroso, formyl, acyl, COOH, carboxylate, alkylcarbonyloxy, carbamoyl, SO3H, sulphonate, sulphamino, sulphamide, amidino, NE1E2, or for unsubstituted or substituted alkyl, alkoxy, alkylamino, alkylthio, alkylsulphinyl, alkylsulphonyl, alkenyl, alkadienyl, alkynyl, cycloalkyl, bicycloalkyl, cycloalkenyl, heterocycloalkyl, aryl or heteroaryl, wherein E1 and E2, independently of one another, stand for hydrogen, alkyl, cycloalkyl or aryl, wherein in each case two adjacent radicals R5 to R8, together with the carbon atom of the benzene nucleus to which they are bound, may also stand for a condensed ring system containing 1, 2 or 3 further rings, and the radicals R1 to R4, where provided, which do not stand for CN or for a phthalimide radical of general formula (II), are selected independently of one another from hydrogen, fluorine, chlorine, bromine, cyano, nitro, nitroso, formyl, acyl, COOH, carboxylate, alkylcarbonyloxy, carbamoyl, SO3H, sulphonate, sulphamino, sulphamide, amidino, NE3E4, or unsubstituted or substituted alkyl, alkoxy, alkylamino, alkylthio, alkylsulphinyl, alkylsulphonyl, alkenyl, alkadienyl, alkynyl, cycloalkyl, bicycloalkyl, cycloalkenyl, heterocycloalkyl, aryl or heteroaryl, wherein E3 and E4, independently of one another, stand for hydrogen, alkyl, cycloalkyl or aryl, wherein R1 and R2 and/or R3 and R4, together with the carbon atom of the quinone ring to which they are bound, may also stand for a condensed ring system containing 1, 2 or 3 further rings.

DETAILED DESCRIPTION OF EMBODIMENTS

Figure 1:
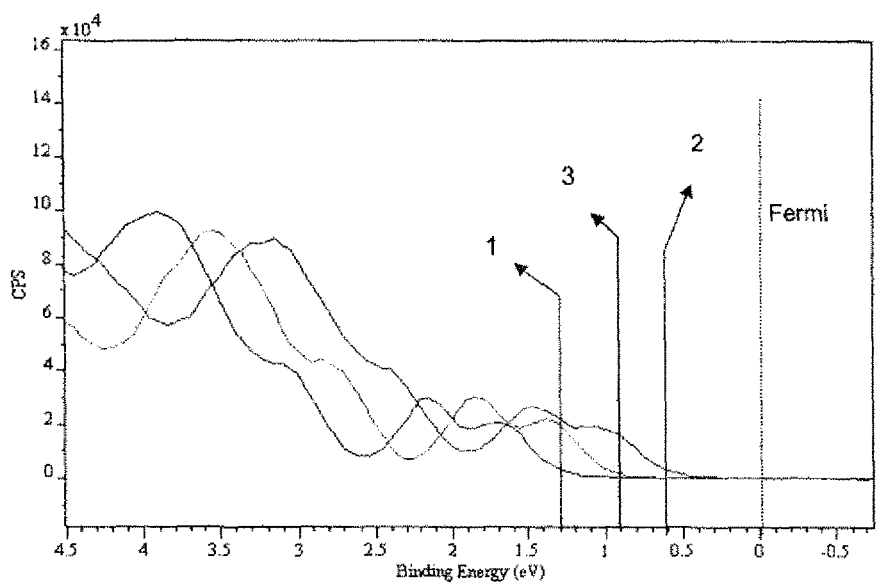
FIG. 1 depicts the diffusion measurement of the compound $F_6TNAP$ compared to UPS.

Within the scope of the present invention, the term "alkyl" includes straight-chain or branched alkyl. It is preferably a straight-chain or branched C1-C30 alkyl, in particular C1-C20 alkyl and most preferably C1-C12 alkyl. In particular, examples of alkyl groups are methyl, ethyl, n-propyl, isopropyl, n-butyl, isobutyl, sec.-butyl, tert.-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

The term "alkyl" also includes alkyl radicals, of which the carbon chains can be interrupted by one or more groups which are not adjacent and which are selected from —O—, —S—, —NRe—, —C(=O)—, —S(=O)— and/or —S(=O)2-. Re preferably stands for hydrogen, alkyl, cycloalkyl, heterocycloalkyl, aryl or hetaryl. The term "alkyl" also includes substituted alkyl radicals. Depending on the length of the alkyl chain, substituted alkyl groups may contain one or more (for example 1, 2, 3, 4, 5 or more than 5) substituents. These are preferably selected independently of one another from cycloalkyl, heterocycloalkyl, aryl, hetaryl, halogen, hydroxyl, mercapto, COOH, carboxylate, SO3H, sulphonate, NE1E2, nitro and cyano, wherein E1 and E2, independently of one another, stand for hydrogen, alkyl, cycloalkyl, heterocycloalkyl, aryl or hetaryl. Halogen substituents are preferably fluorine, chlorine or bromine.

Carboxylate and sulphonate stand for a derivative of a carboxylic acid function or a sulphonic acid function, in particular for a metal carboxylate or a metal sulphonate, a carboxylic acid ester function or a sulphonic acid ester function, or a carboxylic acid amide function or a sulphonic acid amide function. Cycloalkyl, heterocycloalkyl, aryl and hetaryl substituents of the alkyl groups may, for their part, be unsubstituted or substituted; suitable substituents are those named hereinafter for these groups.

The statements made above relating to alkyl also apply to the alkyl parts in alkoxy, alkylamino, alkylthio, alkylsulphinyl, alkylsulphonyl, alkylcarbonyloxy, etc.

Alkyl radicals substituted by aryl ("aralkyl") contain at least one unsubstituted or substituted aryl group, as defined hereinafter. The alkyl group in "aralkyl" may carry at least one further substituent and/or be interrupted by one or more groups, which are not adjacent and which are selected from —O—, —S—, —NRe—, —CO— and/or —SO2-. Aralkyl preferably stands for phenyl C1-C10 alkyl, more preferably for phenyl C1-C4 alkyl, for example for benzyl, 1-phenethyl, 2-phenethyl, 1-phenprop-1-yl, 2-phenprop-1-yl, 3-phenprop-1-yl, 1-phenbut-1-yl, 2-phenbut-1-yl, 3-phenbut-1-yl, 4-phenbut-1-yl, 1-phenbut-2-yl, 2-phenbut-2-yl, 3-phenbut-2-yl, 4-phenbut-2-yl, 1-(phenmeth)-eth-1-yl, 1-(phenmethyl)-1-(methyl)-eth-1-yl or -(phenmethyl)-1-(methyl)-prop-1-yl; preferably for benzyl and 2-phenethyl.

Within the meaning of the present invention, the term "alkenyl" includes straight-chain and branched alkenyl groups which may carry one or more non-cummulated carbon-carbon double bonds (for example 1, 2, 3, 4 or more than 4) depending on the chain length. Alkenyl which contains two double bonds will also be referred to hereinafter as alkadienyl. C2-C18 alkenyl groups are preferred, and C2-C12 alkenyl groups are more preferred. The term "alkenyl" also includes substituted alkenyl groups which may carry one or more (for example 1, 2, 3, 4, 5 or more than 5) substituents. For example, suitable substituents are selected from cycloalkyl, heterocycloalkyl, aryl, hetaryl, halogen, hydroxyl, mercapto, COOH, carboxylate, SO3H, sulphonate, NE3E4, nitro and cyano, wherein E3 and E4, independently of one another, stand for hydrogen, alkyl, cycloalkyl, heterocycloalkyl, aryl or hetaryl.

For example, alkenyl then stands for ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, penta-1,3-dien-1-yl, hexa-1,4-dien-1-yl, hexa-1,4-dien-3-yl, hexa-1,4-dien-6-yl, hexa-1,5-dien-1-yl, hexa-1,5-dien-3-yl, hexa-1,5-lien-4-yl, hepta-1,4-dien-1-yl, hepta-1,4-dien-3-yl, hepta-1,4-dien-6-yl, hepta-1,4-then-7-yl, hepta-1,5-dien-1-yl, hepta-1,5-dien-3-yl, hepta-1,5-dien-4-yl, hepta-1,5-dien-7-yl, hepta-1,6-dien-1-yl, hepta-1,6-dien-3-yl, hepta-1,6-dien-4-yl, hepta-1,6-dien-5-yl, hepta-1,6-dien-2-yl, octa-1,4-dien-1-yl, octa-1,4-dien-2-yl, octa-1,4-dien-3-yl, octa-1,4-dien-6-yl, octa-1,4-dien-7-yl, octa-1,5-dien-1-yl, octa-1,5-dien-3-yl, octa-1,5-dien-4-yl, octa-1,5-dien-7-yl, octa-1,6-dien-1-yl, octa-1,6-dien-3-yl, octa-1,6-dien-4-yl, octa-1,6-dien-5-yl, octa-1,6-dien-2-yl, deca-1,4-dienyl, deca-1,5-dienyl, deca-1,6-dienyl, deca-1,7-dienyl, deca-1,8-dienyl, deca-2,5-dienyl, deca-2,6-dienyl, deca-2,7-dienyl, deca-2,8-dienyl and the like. The statements relating to alkenyl also apply to the alkenyl groups in alkenyloxy, alkenylthio, etc.

The term "alkynyl" includes unsubstituted or substituted alkynyl groups which contain one or more triple bonds which are not adjacent, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The statements relating to alkynyl also apply to the alkynyl groups in alkynyloxy, alkynylthio, etc. Substituted alkynyls preferably carry one or more (for example 1, 2, 3, 4, 5 or more than 5) of the substituents mentioned above for alkyl.

Within the scope of the present invention, the term "cycloalkyl" includes unsubstituted and also substituted cycloalkyl groups, preferably C3-C8 cycloalkyl groups, such as cyclopropyl, cyclobutyl, cyclopentyl, cyclohexyl, cycloheptyl or cyclooctyl, in particular C5-C8 cycloalkyl. Substituted cycloalkyl groups may contain one or more (for example 1, 2, 3, 4, 5 or more than 5) substituents. These are preferably selected independently of one another from alkyl and the substituents mentioned above for the alkyl groups. In the case of substitution, the cycloalkyl groups preferably carry one or more, for example one, two, three, four or five, C1-C6 alkyl groups.

Examples of preferred cycloalkyl groups are cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl, 2-, 3- and 4-sec.-butylcyclohexyl, 2-, 3- and 4-tert-butylcyclohexyl, cycloheptyl, 2-, 3- and 4-methylcycloheptyl, 2-, 3- and 4-ethylcycloheptyl, 2-, 3- and 4-propylcycloheptyl, 2-, 3- and 4-isopropylcycloheptyl, 2-, 3- and 4-butylcycloheptyl, 2-, 3- and 4-sec-butylcycloheptyl, 2-, 3- and 4-tert.-butylcycloheptyl, cyclooctyl, 2-, 3-, 4- and 5-methylcyclooctyl, 2-, 3-, 4- and 5-ethylcyclooctyl and 2-, 3-, 4- and 5-propylcyclooctyl.

The term "cycloalkenyl" includes unsubstituted and substituted monounsaturated hydrocarbon groups containing 3 to 8, preferably 5 to 6 carbon ring members, such as cyclopenten-1-yl, cyclopenten-3-yl, cyclohexen-1-yl, cyclohexen-3-yl, cyclohexen-4-yl and the like. Suitable substituents are those mentioned above for cycloalkyl.

The term "bicycloalkyl" preferably includes bicyclic hydrocarbon radicals containing 5 to 10 C atoms, such as bicyclo[2.2.1]hept-1-yl, bicyclo[2.2.1]hept-2-yl, bicyclo[2.2.1]hept-7-yl, bicyclo[2.2.2]oct-1-yl, bicyclo[2.2.2]oct-2-yl, bicyclo[3.3.0]octyl, bicyclo[4.4.0]decyl and the like.

Within the scope of the present invention, the term "aryl" includes mono- or polynuclear aromatic hydrocarbon radicals, which may be unsubstituted or substituted. Aryl preferably stands for unsubstituted or substituted phenyl, naphthyl, indenyl, fluorenyl, anthracenyl, phenanthrenyl, naphthacenyl, chrysenyl, pyrenyl, etc., and more preferably for phenyl or naphthyl. Substituted aryls may contain one or more (for example 1, 2, 3, 4, 5 or more than 5) substituents, depending on the number and size of their ring systems. These substituents are preferably selected, independently of one another, from alkyl, alkoxy, cycloalkyl, heterocycloalkyl, aryl, hetaryl, halogen, hydroxyl, mercapto, COON, carboxylate, SO3H, sulphonate, NE5E6, nitro and cyano, wherein E5 and E6, independently of one another, stand for hydrogen, alkyl, cycloalkyl, heterocycloalkyl, aryl or hetaryl. Halogen substituents are preferably fluorine, chlorine or bromine. Aryl more preferably stands for phenyl, which in the case of substitution may generally carry 1, 2, 3, 4 or 5, preferably 1, 2 or 3 substituents.

Aryl which carries one or more radicals for example stands for 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert.-butylphenyl, 2,4-, 2,5-, 3,5- and 2,6-di-tert.-butylphenyl and 2,4,6-tri-tert.-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-cyanophenyl.

Within the scope of the present invention, the term "heterocycloalkyl" includes non-aromatic, unsaturated or completely saturated, cycloaliphatic groups generally containing 5 to 8 ring atoms, preferably 5 or 6 ring atoms, in which 1, 2 or 3 of the ring carbon atoms are replaced by heteroatoms selected from oxygen, nitrogen, sulphur and an —NRe—group, and is unsubstituted or substituted by one or more, for example 1, 2, 3, 4, 5 or 6, C1-C6 alkyl groups. Examples of such heterocycloaliphatic groups are pyrrolidinyl, piperidinyl, 2,2,6,6-tetramethyl-piperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 1,2-oxazolin-5-yl, 1,3-oxazolin-2-yl and dioxanyl.

Within the scope of the present invention, the term "heteroaryl" includes unsubstituted or substituted, heteroaromatic, mono- or polynuclear groups, preferably the groups pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl and carbazolyl, wherein these heterocycloaromatic groups may generally carry 1, 2 or 3 substituents in the case of substitution. The substituents are preferably selected from C1-C6 alkyl, C1-C6 alkoxy, hydroxyl, carboxyl, halogen and cyano.

For example, 5- to 7-membered nitrogen-containing heterocycloalkyl or heteroaryl radicals which optionally contain further heteroatoms selected from oxygen and sulphur include pyrrolyl, pyrazolyl, imidazolyl, triazolyl, pyrrolidinyl, pyrazolinyl, pyrazolidinyl, imidazolinyl, imidazolidinyl, pyridinyl, pyridazinyl, pyrimidinyl, pyrazinyl, triazinyl, piperidinyl, piperazinyl, oxazolyl, isooxazolyl, thiazolyl, isothiazolyl, indolyl, quinolinyl, isoquinolinyl or quinaldinyl.

The explanations given above with regard to the terms "cycloalkyl", "aryl", "heterocycloalkyl" and "hetaryl" apply accordingly to the terms "cycloalkoxy", "aryloxy", "heterocycloalkoxy" and "hetaryloxy".

Within the meaning of the present invention, the term "acyl" stands for alkanoyl or aroyl groups generally containing 2 to 11, preferably 2 to 8 carbon atoms, for example for the acetyl, propanoyl, butanoyl, pentanoyl, hexanoyl, heptanoyl, 2-ethylhexanoyl, 2-propylheptanoyl, benzoyl or naphthoyl groups.

The NE1E2, NE3E4, NE5E6 and NE7E8 groups preferably stand for N,N-dimethylamino, N,N-diethylamino, N,N-dipropylamino, N,N-diisopropylamino, N,N-di-n-butylamino, N,N-di-t.-butylamino, N,N-dicyclohexylamino or N,N-diphenylamino.

Carbamoyl stands for groups of formula —CO—NE7E8. A specific example is unsubstituted carbamoyl —CO—NH2. N—(C1-C6) monoalkylated and N,N—(C1-C6) dialkylated carbamoyl groups are more preferred.

Sulphamino stands for groups of formula —NE9-SO3Ra, wherein E8, and Ra, independently of one another, stand for hydrogen, alkyl, cycloalkyl, aryl or hetaryl. A specific example is unsubstituted sulphamino —NH—SO3H.

Sulphamide stands for groups of formula —NE10-SO2-NE11E12, wherein E10, E11 and E12, independently of one another, stand for hydrogen, alkyl, cycloalkyl, aryl or hetaryl. A specific example is unsubstituted sulphamide —NH—SO2-NH2.

Amidino stands for groups of formula —C(=NE13)-NE14E15, wherein E13, E14 and E15, independently of one another, stand for hydrogen, alkyl, cycloalkyl, aryl or hetaryl. A specific example is unsubstituted amidino —C(=NH)—NH2.

Halogen stands for fluorine, chlorine, bromine or iodine.

Condensed ring systems may be aromatic, hydroaromatic and cyclic compounds linked by anellation (fused). Condensed ring systems consist of two, three or more than three rings. Depending on the type of linking, a distinction is made in the case of condensed ring systems between an orthoanellation, that is to say each ring has an edge, or two atoms common with each neighbouring ring, and a peri-anellation, in which one carbon atom belongs to more than two rings.

Fused (anellated) rings may be unsubstituted or substituted. Substituted fused rings preferably contain 1, 2 or 3, in particular 1 or 2 substituents. The substituents are preferably selected from alkyl, alkoxy, fluorine, chlorine, COOH, carboxylate, SO3H, sulphonate, NE5E6, nitro, alkylcarbonyloxy, formyl, acyl and cyano.

M+ stands for a cation equivalent, that is to say for a monovalent cation or the fraction of a polyvalent cation corresponding to a unipositive charge. Alkali metal cations are preferred, in particular NA+, K+ or Li+ ions or ammonium ions.

Specific examples of radicals R1, R2, R3 and R4 which do not stand for hydrogen, CN or for a phthalimide radical of general formula (II), and of radicals R5, R6, R7 and R8 which do not stand for hydrogen or CN are as follows: methyl, ethyl, n-propyl, isopropyl, n-butyl, isobutyl, sec.-butyl, tert.-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl, 2-methoxyethyl, 2-ethoxyethyl, 2-propoxyethyl, 2-butoxyethyl, 3-methoxypropyl, 3-ethoxypropyl, 3-propoxypropyl, 3-butoxypropyl, 4-methoxybutyl, 4-ethoxybutyl, 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxamidecyl and 3,6,9,12-tetraoxatetradecyl; 2-methylthioethyl, 2-ethylthioethyl, 2-propylthioethyl, 2-butylthioethyl, 3-methylthiopropyl, 3-ethylthiopropyl, 3-propylthiopropyl, 3-butylthropropyl, 4-methylthiobutyl, 4-ethylthiobutyl, 4-propylthiobutyl, 3,6-dithiaheptyl, 3,6-dithiaoctyl, 4,8-dithanonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiamidecyl and 3,6,9,12-tetrathiatetradecyl; 2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazamidecyl and 3,6,9,12-tetramethyl-3,6,9,12-tetraazamidecyl; (1-ethylethylidene)aminoethylene, (1-ethylethylidene)aminopropylene, (1-ethylethylidene)aminobutylene, (1-ethylethylidene)aminodecylene and (1-ethylethylidene)aminododecylene; propan-2-on-1-yl, butan-3-on-1-yl, butan-3-on-2-yl and 2-ethylpentan-3-on-1-yl; 2-methylsulphinylethyl, 2-ethylsulphinylethyl, 2-propylsulphinylethyl, 2-isopropylsulphinylethyl, 2-butylsulphinylethyl, 1- and 3-methylsulphinylpropyl, 2- and 3-ethylsulphinylpropyl, 2- and 3-propylsulphinylpropyl, 1- and 3-butylsulphinylpropyl, 2- and 4-methylsulphinylbutyl, 2- and 4-ethylsulphinylbutyl, 2- and 4-propylsulphinylbutyl and 4-butylsulphinylbutyl; 2-methylsulphonylethyl, 2-ethylsulphonylethyl, 2-propylsulphonylethyl, 2-isopropyl sulphonylethyl, 2-butylsulphonylethyl, 2- and 3-methylsulphonylpropyl, 2- and 3-ethylsulphonylpropyl, 2- and 3-propylsulphonylpropyl, 2- and 3-butylsulphonylpropyl, 2- and 4-methylsulphonylbutyl, 2- and 4-ethylsulphonylbutyl, 2- and 4-propylsulphonylbutyl and 4-butylsulphonylbutyl; carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl; sulphomethyl, 2-sulphoethyl, 3-sulphopropyl, 4-sulphobutyl, 5-sulphopentyl, 6-sulphohexyl, 8-sulphooctyl, 10-sulphodecyl, 12-sulphododecyl and 14-sulphotetradecyl; 2-hydroxyethyl, 2- and 3-hydroxypropyl, 3- and 4-hydroxybutyl and 8-hydroxy-4-oxaoctyl; 2-cyanoethyl, 3-cyanopropyl, 3- and 4-cyanobutyl; 2-chloroethyl, 2- and 3-chloropropyl, 2-, 3- and 4-chlorobutyl, 2-bromoethyl, 2- and 3-bromopropyl and 2-, 3- and 4-bromobutyl; 2-nitroethyl, 2- and 3-nitropropyl and 2-, 3- and 4-nitrobutyl; methoxy, ethoxy, propoxy, butoxy, pentoxy and hexoxy; methylthio, ethylthio, propylthio, butylthio, pentylthio and hexylthio; ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8- and 9-decynyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecynyl; ethenyl, 1- and 2-propenyl, 1-, 1- and 3-butenyl, 1-, 2-, 3- and 4-pentenyl, 1-, 2-, 3-, 4- and 5-hexenyl, 1-, 2-, 3-, 4-, 5-, 6-, 7-, 8- and 9-decenyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecenyl; methylamino, ethylamino, propylamino, butylamino, pentylamino, hexylamino, dicyclopentylamino, dicyclohexylamino, dicycloheptylamino, diphenylamino and dibenzylamino; formylamino, acetylamino, propionylamino and benzoylamino; carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl; aminosulphonyl, N-dodecylaminosulphonyl, N,N-dipenylaminosulphonyl, and N,N-bis(4-chlorophenyl)aminosulphonyl; methoxycarbonyl, ethoxycarbonyl, propoxycarbonyl, hexoxycarbonyl, dodecyloxycarbonyl, octadecyloxycarbonyl, phenoxycarbonyl, (4-tert-butylphenoxy)carbonyl and (4-chlorophenoxy)carbonyl; methoxysulphonyl, ethoxysulphonyl, propoxysulphonyl, butoxysulphonyl, hexoxysulphonyl, dodecyloxysulphonyl, octadecyloxysulphonyl, phenoxysulphonyl, 1- and 2-naphthyloxysulphonyl, (4-tert-butylphenoxy)sulphonyl and (4-chlorophenoxy)sulphonyl; diphenylphosphino, di-(o-tolyl)phosphino and diphenylphosphinoxido; fluorine, chlorine and bromine; phenylazo, 2-naphthylazo, 2-pyridylazo and 2-pyrimidylazo; cyclopropyl, cyclobutyl, cycloheptyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec.-butylcyclohexyl, 3- and 4-tert.butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec.-butylcycloheptyl, 3- and 4-tert.- butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl; 1-, 2- and 3-cyclopentenyl, 1-, 2-, 3- and 4-cyclohexenyl, 1-, 2- and 3-cycloheptenyl and 1-, 2-, 3- and 4-cyclooctenyl; 2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl; Phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl; 1-, 2-, 3-, 4-, 5-, 6- and 7-indolyl, 1-, 2-, 3-, 4-, 5-, 6- and 7-isoindolyl, 5-(4-methylisoindolyl), 5-(4-phenylisoindolyl), 1-, 2-, 4-, 6-, 7- and 8-(1,2,3,4-tetrahydroisoquinolinyl), 3-(5-phenyl)-(1,2,3,4-tetrahydroisoquinolinyl), 5-(3-dodecyl-(1,2,3,4-tetrahydroisoquinolinyl), 1-, 2-, 3-, 4-, 5-, 6-, 7- and 8-(1,2,3,4-tetrahydroquinolinyl) and 2-, 3-, 4-, 5-, 6-, 7- and 8-chromanyl, 2-, 4- and 7-quinolinyl, 2-(4-phenylquinolinyl) and 2-(5-ethylquinolinyl); 2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-sec.-butylphenyl, 2,4-, 3,5- and 2,6-di-sec.-butylphenyl and 2,4,6-tri-sec.-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl, and 2-, 3- and 4-butoxyphenyl; 2-, 3- and 4-chlorophenyl, and 2,4-, 3,5- and 2,6-dichlorophenyl; 2-, 3- and 4-hydroxyphenyl and 2,4-, 3,5- and 2,6 dihydroxyphenyl; 2-, 3- and 4-cyanophenyl; 3- and 4-carboxyphenyl; 3- and 4-carboxamidophenyl, 3- and 4-N-methylcarboxamidophenyl and S— and 4-N-ethylcarboxamidophenyl; 3- and 4-acetylaminophenyl, 3- and 4-propionylaminophenyl and 3- and 4-buturylaminophenyl; 3- and 4-N-phenylaminophenyl, 3- and 4-N-(o-tolyl)aminophenyl, 3- and 4-N-(m-tolyl)aminophenyl and 3- and 4-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidypaminophenyl; 4-phenylazophenyl, 4-(1-naphthylazo)phenyl, 4-(2-naphthylazo)phenyl, 4-(4-naphthylazo)phenyl, 4-(2-pyriylazo)phenyl, 4-(4-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl; phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

Preferred fluorine-containing radicals R1 to R8 are as follows: 2,2,2-trifluoroethyl, 2,2,3,3,3-pentafluoropropyl, 2,2-difluoroethyl, 2,2,3,3,4,4,4-heptafluorobutyl, 2,2,3,3,3-pentafluoropropyl, 1H,1H-pentadecafluorooctyl, 3-bromo-3,3-difluoropropyl, 3,3,3-trifluoropropyl, 3,3,3-trifluoropropyl, 1H,1H,2H,2H-perfluorodecyl, 3-(perfluorooctyl)propyl, 4,4-difluorobutyl-, 4,4,4-trifluorobutyl, 5,5,6,6,6-pentafluorohexyl, 2,2-difluoropropyl, 2,2,2-trifluoro-1-phenylethylamino, 1-benzyl-2,2,2-trifluoroethyl, 2-bromo-2,2-difluoroethyl, 2,2,2-trifluoro-1-pyridin-2-yl ethyl, 2,2-difluoropropyl, 2,2,2-trifluoro-1-(4-methoxyphenyl)ethylamino, 2,2,2-trifluoro-1-phenylethyl, 2,2-difluoro-1-phenylethyl, 1-(4-bromophenyl)-2,2,2-trifluoroethyl, 3-bromo-3,3-difluoropropyl, 3,3,3-trifluoropropylamine, 3,3,3-trifluoro-n-propyl, 1H,1H,2H,2H-perfluorodecyl, 3-(perfluorooctyl)propyl, pentafluorophenyl, 2,3,5,6-tetrafluorophenyl, 4-cyano-(2,3,5,6)-tetrafluorophenyl, 4-carboxy-2,3,5,6-tetrafluorophenyl, 2,4-difluorophenyl, 2,4,5-trifluorophenyl, 2,4,6-trifluorophenyl, 2,5-difluorophenyl, 2-fluoro-5-nitrophenyl, 2-fluoro-5-trifluoromethylphenyl, 2-fluoro-5-methylphenyl, 2,6-difluorophenyl, 4-carboxamido-2,3,5,6-tetrafluorophenyl, 2-bromo-4,6-difluorophenyl, 4-bromo-2-fluorophenyl, 2,3-difluorophenyl, 4-chloro-2-fluorophenyl, 2,3,4-trifluorophenyl, 2-fluoro-4-iodphenyl, 4-bromo-2,3,5,6-tetrafluorophenyl, 2,3,6-trifluorophenyl, 2-bromo-3,4,6-trifluorophenyl, 2-bromo-4,5,6-trifluorophenyl, 4-bromo-2,6-difluorophenyl, 2,3,4,5-tetrafluorophenyl, 2,4-difluoro-6-nitrophenyl, 2-fluoro-4-nitrophenyl, 2-chloro-6-fluorophenyl, 2-fluoro-4-methylphenyl, 3-chloro-2,4-difluorophenyl, 2,4-dibromo-6-fluorophenyl, 3,5-dichloro-2,4-difluorophenyl, 4-cyano-2-fluorophenyl, 2-chloro-4-fluorophenyl, 2-fluoro-3-trifluoromethylphenyl, 2-trifluoromethyl-6-fluoro-phenyl, 2,3,4,6-tetrafluorophenyl, 3-chloro-2-fluorophenyl, 5-chloro-2-fluorophenyl, 2-bromo-4-chloro-6-fluorophenyl, 2,3-dicyano-4,5,6-trifluorophenyl, 2,4,5-trifluoro-3-carboxyphenyl, 2,3,4-trifluoro-6-carboxyphenyl, 2,3,5-trifluorophenyl, 4-trifluoromethyl-2,3,5,6-tetrafluorophenyl, 2-fluoro-5-carboxyphenyl, 2-chloro-4,6-difluorophenyl, 6-bromo-3-chloro-2,4-difluorophenyl, 2,3,4-trifluoro-6-nitrophenyl, 2,5-difluoro-4-cyanophenyl, 2,5-difluoro-4-trifluoromethylphenyl, 2,3-difluoro-6-nitrophenyl, 4-trifluoromethyl-2,3-difluorophenyl, 2-bromo-4,6-difluorophenyl, 4-bromo-2-fluorophenyl, 2-nitrotetrafluorophenyl 2,2',3,3',4',5,5',6,6'-nonafluorobiphenyl, 2-nitro-3,5,6-trifluorophenyl, 2-bromo-6-fluorophenyl, 4-chloro-2-fluoro-6-iodphenyl, 2-fluoro-6-carboxyphenyl, 2,4-difluoro-3-trifluorophenyl, 2-fluoro-4-trifluorophenyl, 2-fluoro-4-carboxyphenyl, 4-bromo-2,5-difluorophenyl, 2,5-dibromo-3,4,6-trifluorophenyl, 2-fluoro-5-methylsulphonyl-penyl, 5-bromo-2-fluorophenyl, 2-fluoro-4-hydroxymethylphenyl, 3-fluoro-4-bromomethylphenyl, 2-nitro-4-trifluoromethylphenyl, 4-trifluoromethylphenyl, 2-bromo-4-trifluoromethylphenyl, 2-bromo-6-chloro-4-(trifluoromethyl)phenyl, 2-chloro-4-trifluoromethylphenyl, 3-nitro-4-(trifluoromethyl)phenyl, 2,6-dichloro-4-(trifluoromethyl)phenyl, 4-trifluorophenyl, 2,6-dibromo-4-(trifluoromethyl)phenyl, 4-trifluoromethyl-2,3,5,6-tetrafluorophenyl, 3-fluoro-4-trifluoromethylphenyl, 2,5-difluoro-4-trifluoromethylphenyl, 3,5-difluoro-4-trifluoromethylphenyl, 2,3-difluoro-4-trifluoromethylphenyl, 2,4-bis(trifluoromethyl)phenyl, 3-chloro-4-trifluoromethylphenyl, 2-bromo-4,5-di(trifluoromethyl)phenyl, 5-chloro-2-nitro-4-(trifluoromethyl)phenyl, 2,4,6-tris(trifluoromethyl)phenyl, 3,4-bis(trifluoromethyl)phenyl, 2-fluoro-3-trifluoromethylphenyl, 2-iod-4-trifluoromethylphenyl, 2-nitro-4,5-bis(trifluoromethyl)phenyl, 2-methyl-4-(trifluoromethyl)phenyl, 3,5-dichloro-4-(trifluoromethyl)phenyl, 2,3,6-trichloro-4-(trifluoromethyl)phenyl, 4-(trifluoromethyl)benzyl, 2-fluoro-4-(trifluoromethyl)benzyl, 3-fluoro-4-(trifluoromethyl)benzyl, 3-chloro-4-(trifluoromethyl)benzyl, 4-fluorophenethyl, 3-(trifluoromethyl)phenethyl, 2-chloro-6-fluorophenethyl, 2,6-dichlorophenethyl, 3-fluorophenethyl, 2-fluorophenethyl, (2-trifluoromethyl)phenethyl, 4-fluorophenethyl, 3-fluorophenethyl, 4-trifluoromethylphenethyl, 2,3-difluorophenethyl, 3,4-difluorophenethyl, 2,4-difluorophenethyl, 2,5-difluorophenethyl, 3,5-difluorophenethyl, 2,6-difluorophenethyl, 4-(4-fluorophenyl)phenethyl, 3,5-di(trifluoromethyl)phenethyl, pentafluorophenethyl, 2,4-di(trifluoromethyl)phenethyl, 2-nitro-4-(trifluoromethyl)phenethyl, (2-fluoro-3-trifluoromethyl)phenethyl, (2-fluoro-5-trifluoromethyl)phenethyl, (3-fluoro-5-trifluoromethyl)phenethyl, (4-fluoro-2-trifluoromethyl)phenethyl, (4-fluoro-3-trifluoromethyl)phenethyl, (2-fluoro-6-trifluoromethyl)phenethyl, (2,3,6-trifluoro)phenethyl, (2,4,5-trifluoro)phenethyl, (2,4,6-trifluoro)phenethyl, (2,3,4-trifluoro)phenethyl, (3,4,5-trifluoro)phenethyl, (2,3,5-trifluoro)phenethyl, (2-chloro-5-fluoro)phenethyl, (3-fluoro-4-trifluoromethyl)phenethyl, (2-chloro-5-trifluoromethyl)phenethyl, (2-fluoro-3-chloro-5-trifluoromethyl)phenethyl, (2-fluoro-3-chloro)phenethyl, (4-fluoro-3-chloro)phenethyl, (2-fluoro-4-chloro)phenethyl, (2,3-difluoro-4-methyl)phenethyl-, 2,6-difluoro-3-chlorophenethyl, (2,6-difluoro-3-methyl)phenethyl, (2-trifluoromethyl-5-chloro)phenethyl, (6-chloro-2-fluoro-5-methyl)phenethyl, (2,4-dichloro-5-fluoro)phenethyl, 5-chloro-2-fluorophenethyl, (2,5-difluoro-6-chloro)phenethyl, (2,3,4,5-tetrafluoro)phenethyl, (2-fluoro-4-trifluoromethyl)phenethyl, 2,3-(difluoro-4-trifluoromethyl)phenethyl, (2,5-di(trifluoromethyl))phenethyl, 2-fluoro-3,5-dibromophenethyl, (3-fluoro-4-nitro)phenethyl, (2-bromo-4-trifluoromethyl)phenethyl, 2-(bromo-5-fluoro)phenethyl, (2,6-difluoro-4-bromo)phenethyl, (2,6-difluoro-4-chloro)phenethyl, (3-chloro-5-fluoro)phenethyl, (2-bromo-5-trifluoromethyl)phenethyl and the like.

In a specific embodiment none of the radicals R1 to R4 in the quinone derivatives of formula (I) stands for halogen.

In a further specific embodiment the radicals R1 to R4 in the quinone derivatives of formula (I) are only selected from CN and phthalimide radicals of general formula (II).

In a further specific embodiment two of the radicals R1 to R4 in the quinone derivatives of formula (I) stand for cyano. R1 and R2 or R3 and R4 thus stand specifically for cyano.

In a further specific embodiment two of the radicals R1 to R4 in the quinone derivatives of formula (I) stand for a phthalimide radical of general formula (II). R1 and R2 or R3 and R4 thus stand specifically for a phthalimide radical of general formula (II).

The quinone derivatives of general formula (I) preferably contain at least one phthalimide radical of general formula (II), wherein none of the radicals R5 to R8 stands for halogen. In a specific embodiment the quinone derivatives of general formula (I) contain only phthalimide radicals of general formula (II), wherein none of the radicals R5 to R8 stands for halogen.

The quinone derivatives of general formula (I) preferably contain at least one phthalimide radical of general formula (II), wherein the radicals R5 to R8 stand for hydrogen. In a specific embodiment the quinone derivatives of general formula (I) contain only phthalimide radicals of general formula (II), wherein the radicals R5 to R8 stand for hydrogen.

A preferred quinone derivative (I) is the compound of general formula (I.A)

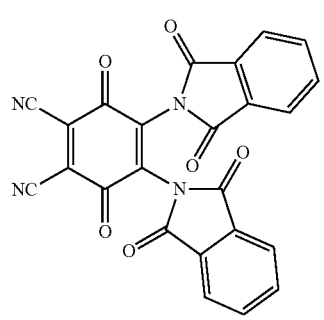

(I.A)

Acceptable quinone compounds which are suitable as starting materials for production of the quinone derivatives (I) according to the invention and used in accordance with the invention are commercially obtainable or are obtainable by methods known to the person skilled in the art. For example, the corresponding halogenated, specifically chlorinated quinines such as 2,3-dichloro-5,6-dicyano-p-benzoquinone (DDQ) are suitable as starting materials. For example, the synthesis of the compound (I.A) is thus achieved by reacting DDQ with potassium phthalimide in accordance with the following scheme 1:

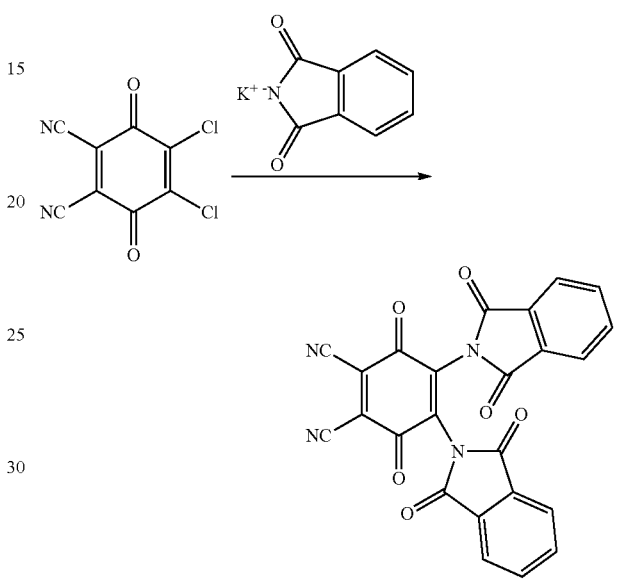

The invention therefore further relates to a method for producing quinine derivatives of general formula (I)

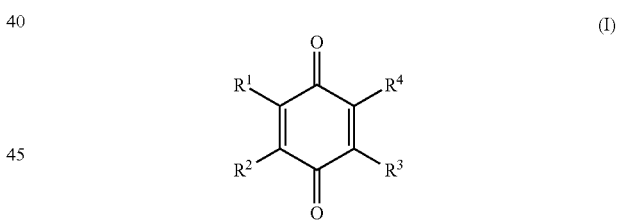

(I)

wherein R1 to R4 are as defined above,
in which a compound of formula (I), in which at least one of the radicals R1 to R4 stands for Cl or Br, is reacted with a phthalimide compound of general formula (II.a)

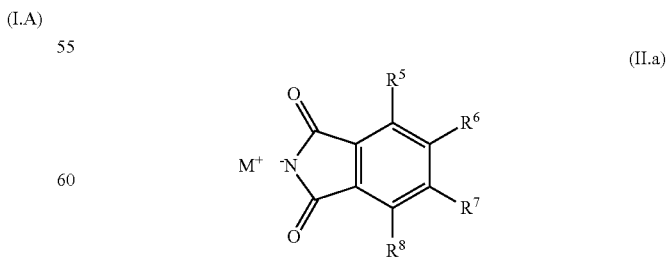

(II.a)

wherein
M+ stands for a cation equivalent, and
R5, R6, R7 and R8 are as defined above.

For reaction with the phthalimide compound of general formula (II.a), a compound of formula (I) is preferably used in which the halogen radicals R1 to R4 stand for Cl.

The phthalimide salt (II.a) is produced starting from the corresponding phthalimide by reaction with a base, preferably an alkali metal hydroxide or alkaline earth metal hydroxide. Examples of suitable alkali metal or alkaline earth metal hydroxides are NaOH, KOH, Ca(OH)2, etc. In an advantageous embodiment an alcohol alkali metal hydroxide solution is used.

The quinone derivatives of general formula (I) are generally produced in the presence of a solvent which is inert under reaction conditions. Such solvents include aromatic solvents such as toluene or xylene, or polar aprotic solvents. Suitable polar aprotic solvents are acetonitrile, dimethylformamide, dimethylacetamide, dimethylsulphoxide and nitrogen heterocycles, such as pyridine, pyrimidine, quinoline, isoquinoline, quinaldine, N-methylpiperidine, N-methylpiperidone and N-methylpyrrolidone. Mixtures of the aforementioned solvents are also suitable.

The reaction temperature is generally ambient temperature to 200° C., preferably 40° C. to 160° C., more preferably 50° C. to 150° C.

The molar ratio of phtalimide anion to the number of halogen atoms to be substituted is preferably approximately 1:1 (that is to say, for example, approximately 0.9:1 to 1:1). It is generally also desirable to replace only some of the halogen atoms with phthalimide groups.

If desired, the quinone derivatives (I) may be subjected to at least one processing step. This includes cleaning by conventional methods known to the person skilled in the art, for example by crystallisation or sublimation. For a use of the products as a dopant, for example for semiconductor materials, it may be advantageous to clean the products by sublimation.

The quinone derivatives according to the invention of general formula (I) are characterised by at least one of the following advantageous properties:
good accessibility by simple synthesis methods,
high thermal stability,
good prospects for sublimation,
low tendency for migration (diffusion) of the dopant into adjacent, undoped layers,
homogeneous distribution of the dopant in the material doped therewith,
high electron affinity when used as a p-dopant,
long service life of the electronic components produced therefrom, especially OLEDs.

The quinone derivatives according to the invention of general formula (I) are outstandingly suitable as dopants in organic electronics. They are specifically used as dopants for organic semiconductive materials. Organic semiconductive materials which contain at least one quinone derivative according to the invention of general formula (I) are advantageously suitable for the production of electronic components. Such components include, above all, organic light-emitting diodes (OLEDs), organic field-effect transistors (OFETs) and organic photovoltaics.

The quinone derivatives according to the invention of general formula (I) are particularly suitable as p-dopants for a hole conductor material.

The effect of the dopant on a semiconductor material can be measured, for example, by means of UPS (ultra-violet photoelectron spectroscopy). For example, this makes it possible to demonstrate the influence of the doping on the energy difference between the Fermi level and the HOMO level.

The quinone derivatives according to the invention of general formula (I) are also suitable as dopants for charge transport materials.

Suitable p-dopable materials, which can be doped with at least one quinone derivative according to the invention of general formula (I), are essentially the organic donor semiconductor materials known to the person skilled in the art. These include:

Phthalocyanines, which are not halogenated or are halogenated. These include metal-free or divalent metals or phthalocyanines containing metal-atom-containing groups, in particular those of titanyloxy, vanadyloxy, iron, copper, zinc, etc. In particular, suitable phthalocyanines are copper phthalocyanine, zinc phthalocyanine and metal-free phthalocyanine. For example, suitable halogenated phthalocyanines are 2,6,10,14-tetrafluorophthalocyanine, for example 2, 6,10,14-tetrafluoro copper pthalocyanine and 2,6,10,14-tetrafluoro zinc phthalocyanine; 1,5,9,13-tetrafluorophthalocyanine, for example 1, 5,9,13-tetrafluoro copper phthalocyanine and 1,5, 9,13-tetrafluoro zinc phthalocyanine; 2,3,6,7,10,11,14,15-octafluorophthalocyanine, for example 2,3,6,7,10,11,14,15-octafluoro copper phthalocyanine and 2,3,6,7,10,11,14,15-octafluoro zinc phthalocyanine.

Porphyrines, such as 5,10,15,20-tetra(3-pyridyl)porphyrine (TpyP), or else tetrabenzoporphyrines, such as metal-free tetrabenzoporphyrine, copper tetrabenzoporphyrine or zinc tetrabenzoporphyrine.

Acenes, such as anthracene, tetracene and pentacene, which may each be unsubstituted or substituted. Substituted acenes preferably contain at least one substituent which is selected from electron-donating substituents (for example alkyl, alkoxy, ester, carboxylate or thioalkoxy), electron-withdrawing substituents (for example halogen, nitro or cyano) and combinations thereof. These include 2,9-dialkylpentacenes and 2,10-dialkylpentacenes, 2,10-dialkoxypentacenes, 1,4,8,11-tetraalkoxypentacenes and rubrene (5,6,11,12-tetraphenylnaphtacene). Suitable substituted pentacenes are described in US 2003/0100779 and U.S. Pat. No. 6,864,396, to which reference is made here. A preferred acene is rubrene.

Coronenes, such as hexabenzocoronene (HBC-PhCl2), coronene diimide, or triphenylene, such as 2,3,6,7,10,11-hexahexylthiotriphenylene (HTT6), 2,3,6,7,10,11-hexakis-(4-n-nonylphenyl)triphenylene (PTP9) or 2,3,6,7,10,11-hexakis-(undecyloxy)triphenylene (HAT11).

Thiophenes, oligothiophenes and substituted derivatives thereof. Suitable oligothiophenes are quaterthiophenes, quinquethiophenes, sexithiophenes, $\alpha,\omega$-di(C1-C8)alkyloligothiophenes such as $\alpha,\omega$-dihexylquaterthiophenes, $\alpha,\omega$-dihexylquinquethiophenes and $\alpha,\omega$-dihexylsexithiophenes, poly (alkylthiophenes) such as poly(3-hexylthiophene), bis (dithienothiophenes), anthradithiophenes and dialkylanthradithiophenes such as dihexylanthradithiophene, phenylene-thiophene (P-T) oligomers and derivatives thereof, especially $\alpha,\omega$-alkyl-substituted phenylene-thiophene oligomers.

Compounds of the type $\alpha,\alpha'$-bis(2,2-dicyanovinyl)quinquethiophene (DCV5T), 3-(4-octylphenyl)-2,2'-bithiophene (PTOPT), poly(3-(4'-(1,4,7-trioxaoctyl)phenyl)thiophene (PEOPT), poly(3-(2'-methoxy-5'-octylphenyl)thiophene)) (POMeOPT), and poly(3-octylthiophene) (P3OT), poly(pyridopyrazinevinylene)-polythiophene blends such as EHH-PpyPz, PTPTB, BBL, F8BT and PFMO copolymers (see Brabec C., Adv. Mater., 2996, 18, 2884) and (PCPDTBT) poly[2,6-(4,4-bis(2-ethylhexyl)-4H-cyclopenta[2,1-b;3,4-b']-dithiophene)-4,7-(2,1,3-benzothiadiazole)] are also suitable.

Paraphenylene vinylene and oligomers or polymers containing paraphenylene vinylene, for example polyparaphenylene vinylene, MEH-PPV (poly(2-methoxy-5-(2'-ethylhexyloxy)-1,4-phenylenevinylene)), MDMO-PPV (poly(2-methoxy-5-(3',7'-dimethyloctyloxy)-1,4-phenylene vinylene)), PPV, and CN-PPV (with various alkoxy derivatives).

Phenylene ethynylene/phenylene vinylene hybrid polymers (PPE-PPV).

Polyfluorenes and alternating polyfluorene copolymers, for example with 4,7-dithien-2'-yl-2,1,3-benzothiadiazole. Poly(9,9'-dioctylfluorene-co-benzothiadiazole) (F8BT), poly(9,9'-dioctylfluorene-co-bis(N,N'-(4-butylphenyl))-bis(N,N'-phenyl)-1,4-phenylenediamine (PFB) are also suitable.

Polycarbazoles, that is to say oligomers and polymers containing carbazole.

Polyanilines, that is to say oligomers and polymers containing aniline.

Triarylamines, polytriarylamines, polycyclopentadienes, polypyrroles, polyfurans, polysiloles, polyphospholes, TPD, CBP, Spiro-MeOTAD. Triphenylamine derivatives, particularly N,N'-bis-1-(naphthyl)-N,N'-diphenyl-1,1'-biphenyl-4,4'-diamine (NPD) and 4,4'-bis(carbazol-9-yl)biphenyl (CBP) are preferred.

Further materials suitable for doping, particularly organic donor semiconductor materials, wilt also be named hereinafter with regard to the individual electronic components to which reference is made here.

The ratio by weight dopant to material to be doped is preferably equal to or less than 1:1, more preferably equal to or less than 0.5:1, in particular equal to or less than 0.1:1. The ratio by weight dopant to material to be doped is particularly in a range of 0.000001:1 to 2:1, more particularly in a range of 0.00001:1 to 1:1, even more particularly in a range of 0.0001:1 to 0.1:1.

The material to be doped with the quinone compounds (I) according to the invention can be doped by one or a combination of the following methods:
  a) co-evaporation under vacuum with one source for the material to be doped and one for the dopant;
  b) sequential deposition of the material to be doped and of the dopant on a substrate with subsequent inward diffusion of the dopant, in particular by thermal treatment;
  c) doping of a layer of the material to be doped by a solution of dopant with subsequent evaporation of the solvent, in particular by thermal treatment;
  d) surface doping of a material layer to be doped by applying a layer of dopant over the surface;
  e) production of a solution of material to be doped and dopant and subsequent production of a layer formed of this solution by means of conventional methods, for example evaporation of the solvent or spin coating.

P-doped organic semiconductors can thus be produced which can be used in a versatile manner.

The invention further relates to an organic light-emitting diode (OLED) containing at least one quinone derivative of general formula (I), as defined above. The organic light-emitting diode contains the quinone derivative (I), preferably in a conductor layer, particularly in a hole conductor layer.

A typical organic light-emitting diode contains an anode (An), a cathode (Ka) and a light-emitting layer (E) arranged between the anode (An) and the cathode (Ka). A typical organic light-emitting diode additionally optionally contains at least one blocking layer for holes and/or excitons.

The organic light-emitting diodes (OLEDs) according to the invention thus preferably have the following structure: an anode (An), a cathode (Ka) and a light-emitting layer (E) arranged between the anode (An) and the cathode (Ka) as well as optionally at least one blocking layer for holes/excitons.

For example, the OLED according to the invention may be formed in a preferred embodiment from the following layers:
  1. anode
  2. hole conductor layer
  3. light-emitting layer
  4. blocking layer for holes/excitons
  5. electron conductor layer
  6. cathode Layer sequences different from the above-mentioned structure are also possible and are known to the person skilled in the art. For example, it is possible that the OLEDs do not all comprise the aforementioned layers, for example an OLED with the layers (1) (anode), (3) (light-emitting layer) and (6) (cathode) is also suitable, wherein the functions of the layers (2) (hole conductor layer) and (4) (blocking layer for holes/excitons) and (5) (electron conductor layer) are carried out by the adjacent layers. OLEDs which comprise the layers (1), (2), (3) and (6) or the layers (1), (3), (4), (5) and (6) are also suitable. Furthermore, the OLEDs between the anode (1) and the hole conductor layer (2) may comprise a blocking layer for electrons/excitons.

It is also possible that a plurality of the aforementioned functions (electron/exciton blocker, hole/exciton blocker, hole injection, hole conduction, electron injection, electron conduction) are combined in one layer and, for example, are carried out by a single material present in this layer. For example, a material used in the hole conductor layer may, in one embodiment, simultaneously block excitons and/or electrons.

Furthermore, the individual aforementioned layers of the OLED may in turn be formed of two or more layers. For example, the hole conductor layer may be formed of a layer into which holes are injected from the electrode, and a layer which transports the holes away from the hole-injecting layer into the light-emitting layer. The electron conduction layer may also consist of a plurality of layers, for example a layer in which electrons are injected by the electrode, and a layer which obtains electrons from the electron injection layer and transports them into the light-emitting layer.

In a specific embodiment the OLED according to the invention contains a hole conductor layer which contains at least one quinone derivative according to the invention of formula (I) as a dopant. This doped hole conductor layer may be used as a single hole conductor layer or in combination with at least one further undoped or doped hole conductor layer.

The aforementioned layers are each selected in accordance with factors such as energy level, temperature resistance and charge carrier mobility, as well as the energy difference between the aforementioned layers and the organic layers or the metal electrodes. The person skilled in the art is able to select the structure of the OLEDs in such a way that it is optimally adapted to the compounds used as emitter substances.

In order to obtain particularly efficient OLEDs, the HOMO (highest occupied molecular orbital) of the hole conductor layer should, for example, be approximated with the working function of the anode, and the LUMO (lowest unoccupied molecular orbital) of the electron conductor layer should be approximated with the working function of the cathode, provided the aforementioned layers are present in the OLEDs according to the invention.

The anode (1) is an electrode which provides positive charge carriers. For example, it may be formed of materials which contain a metal, a mixture of different metals, a metal alloy, a metal oxide or a mixture of different metal oxides. Alternatively, the anode may be a conductive polymer. Suitable metals include the metals of groups Ib, Iva, Va and VIa of the Periodic Table of the Chemical Elements as well as the transition metals of group VIIIa. If the anode is to be permeable to light, mixed metal oxides of groups IIb, IIIb and IVb of the Periodic Table of the Chemical Elements (old IUPAC version) are generally used, for example indium tin oxide (ITO). It is also possible that the anode (1) contains an organic material, for example polyaniline, for example as described in Nature, Vol. 357, pages 477 to 479 (11 Jun. 1992). At least either the anode or the cathode should be transparent at least in part so as to be able to decouple the light foil led. ITO is preferably used as material for the anode (1).

In addition to those mentioned above, suitable hole conductor materials for the layer (2) and optionally further hole-conducting layers of the OLEDs according to the invention are disclosed for example in Kirk-Othmer Encyclopaedia of Chemical Technology, 4th edition, vol. 18, pages 837 to 860, 1996. Both hole-transporting molecules and polymers can be used as hole transport material. Hole-transporting molecules used conventionally are selected from the group consisting of N,N-bis-1-(naphthyl)-N,N'-diphenyl-1,1'-biphenyl-4,4'-diamine (NPD) and 4,4'-bis(carbazol-9-yl)biphenyl (CBP), tris[N-(1-naphthyl)-N-(phenylamino)]triphenylamine (1-NaphDATA), 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N-bis(4-methylphenyl)-N,N'-bis(4-ethylphenyl)-[1,1'-(3,3'-dimethyl)biphenyl]-4,4'-diamine (ETPD), tetrakis(3-methyl-phenyl)-N,N,N',N'-2,5-phenylenediamine (PDA), α-phenyl-4-N,N-diphenylaminostyrene (TPS), p-(diethylamino)benzaldehyde diphenyl hydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4"-tris(N,N-diphenylamino)triphenylamine (TDTA), 4,4',4"-tris(N,N-diphenylamino)triphenylamine (TDTA), 4,4',4"-tri(N-carbazolyl)triphenylamine (TCTA), N,N'-bis(naphthalene-2-yl)-N,N'-bis(phenyl)-benzidine (β-NPB), N,N'-bis(3-methylphenyl)-N,N'-bis(phenyl)-9,9-spirobifluorene (Spiro-TPD), N,N'-bis(naphthalene-1-yl)-N,N'-bis(phenyl)-9,9-spirobifluorene (Spiro-NPB), N,N'-bis(3-methylphenyl)-N,N'-bis(phenyl)-9,9-dimethyl fluorene (DMFL-TPD), N,N'-bis(3-methylphenyl)-N,N'-bis(phenyl)-9,9-diphenylfluorene (DPFL-TPD), N,N'-bis(napthalen-1-yl)-N,N'-bis(phenyl)-9,9-diphenylfluorene (DPFL-NPB), 2,2',7,7'tetrakis(N,N-diephenylamino)-9,9'-spirobifluorene (Spiro-TAD), 9,9-bis[4-N,N-bis-biphenyl-4-yl-amino)phenyl]-9H-fluorene (BPAPF), 9,9-bis[4-(N,N-bis-naphthalene-2-yl-amino)phenyl]-9H-fluorene (NPAPF), 9,9-bis[4-(N,N-bis-naphthalen-2-yl-N,N'-bis-phenyl-amino)phenyl]-9H-fluorene (NPBAPF), 2,2',7,7'-tetrakis[N-naphthalenyl(phenyl)amino]-9,9'-spirobifluorene (Spiro-2NPB), N,N'-bis(phenanthren-9-yl)-N,N'-bis(phenyl)benzidine (PAPB), 2,7-bis[N,N-bis(9,9-spirobifluoren-2-yl)amino]-9,9-spirobifluorene (Spiro-5), 2,2'-bis[N,N-bis(biphenyl-4-yl)amino]-9,9-spirobifluorene (2,2'-Spiro-DBP), 2,2'-bis(N,N-diphenylamino)-9,9-spirobifluorene (Spiro-BPA), 2,2',7,7'-tetra(N,N-ditolyl)amino-spirobifluorene (Spiro-TTB), N,N,N',N'-tetranaphthalen-2-yl-benzidine (TNB), porphyrine compounds and phthalocyanines such as copper phthalocyanines. Hole-transporting polymers conventionally used are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above.

Furthermore, in one embodiment, it is possible to use carbene complexes as hole conductor materials, the band gap of the at least one hole conductor material generally being greater than the band gap of the emitter material used. Within the meaning of the present application, "band gap" is understood to mean the triplet energy. Suitable carbene complexes are, for example, carbene complexes as described in WO 2005/019373 A2, WO 2006/056418 A2, WO 2005/113704, WO 2007/115970, WO 2007/115981 and WO 2008/000727. One example of a suitable carbene complex is Ir(dpbic)3 with the formula:

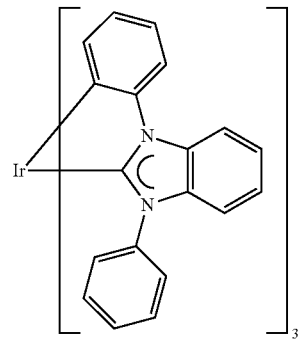

which is disclosed, for example, in WO2005/019373.

The light-emitting layer (3) contains at least one emitter material. In principle, it may be a fluorescence or phosphorescence emitter, suitable emitter materials being known to the person skilled in the art. The at least one emitter material is preferably a phosphorescence emitter. The phosphorescence emitter compounds preferably used are based on metal complexes, wherein in particular the complexes of the metals Ru, Rh, Ir, Pd and Pt, especially the complexes of Ir, have gained in significance.

Suitable metal complexes for use in the OLEDs according to the invention are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301A1, WO 2006/067074 A1, WO 2006/056418, WO 2006121811A1, WO 2007095118 A2, WO 2007/115970, WO 2007/115981 and WO 2008/000727.

Further suitable metal complexes are the commercially available metal complexes tris(2-phenylpyridine)iridium (III), iridium(III)tris(2-(4-tolyl)pyridinato-N,C2'), iridium(III)tris (1-phenylisoquinoline), iridium(III)bis(2,2'-benzothienyl)pyridinato-N,C3')(acetylacetonate), iridium(III) bis(2-(4,6-difluorophenyl)pyridinato-N,C2)picolinate, iridium(III)bis(1-phenylisoquinoline)(acetylacetonate), iridium(III)bis(di-benzo[f,h]quinoxaline)(acetylacetonate), iridium(III)bis(2-methyldi-benzo[f,h]quinoxaline)(acetylacetonate) and tris(3-methyl-1-phenyl-4-trimethylacetyl-5-pyrazoline)terbium(III).

Furthermore, the following commercially available materials are suitable: tris(dibenzoylacetonato)mono(phenanthroline)europium(III), tris(dibenzoylmethane)mono (phenanthroline)europium(III), tris(dibenzoylmethane)mono(5-aminophenan-throline) europium(III), tris(di-2-naphthoylmethane)mono(phenanthroline)europium(III) tris (4-bromobenzoylmethane)mono(phenanthroline)europium (III) tris(di(biphenyl)-methane) mono(phenanthroline) europium(III), tris(dibenzoylmethane)mono(4,7-diphenylphenanthroline) europium(III), tris (dibenzoylmethane)mono(4,7-dimethyl-phenanthroline) europium(III), tris(dibenzoylmethane)mono(4,7-dimethylphenanthroline disulphonic acid)europium(III) disodium salt, tris[di(4-(2-(2-ethoxyethoxy)ethoxy)benzoylmethane)]mono(phenanthroline) europium(III) and tris[d][4-(2-(2-ethoxyethoxy)ethoxy)benzoylmethane)]mono(5-aminophenanthroline)europium(III).

Suitable triplet emitters are, for example, carbene complexes. In one embodiment of the present invention, the compounds of formula (I) or (Ib) are used in the light-emitting layer as a matrix material together with carbene complexes as triplet emitters. Suitable carbene complexes are known to the person skilled in the art and are described, for example, in WO 2005/019373 A2, WO 2006/056418 A2, WO 2005/113704, WO 2007/115970, WO 2007/115981 and WO 2008/000727.

The light-emitting layer may comprise further components in addition to the emitter material. For example, a fluorescent dye may be present in the light-emitting layer in order to alter the emission colour of the emitter material. Furthermore, in a preferred embodiment a matrix material can be used. This matrix material may be a polymer, for example poly(N-vinylcarbazole) or polysilane. The matrix material may, however, likewise be a small molecule, for example 4,4'-N,N'-dicarbazole biphenyl (CDP=CBP) or tertiary aromatic amines, for example TCTA.

Suitable metal complexes for use as matrix materials and/or hole/exciton blocker materials in OLEDs are also, for example, carbene complexes as described in documents WO 2005/019373 A2, WO 2006/056418, WO 2005/113704, WO 2007/115970, WO 2007/115981 and WO 2008/000727. Explicit reference is made here to the disclosure of the WO applications cited.

If the OLED has a blocking layer for holes, this layer comprises hole blocker materials typically used in OLEDs, such as 2,6-bis(N-carbazolyl)pyridines (mCPy), 2,9-dim ethyl-4,7-diphenyl-1,10-phenanthroline (bathocuproine, (BCP)), bis-(2-methyl-8-quinolinato)-4-phenylphenylato) aluminium(III) (BAlq), phenothiazine-S,S-dioxide derivates and 1,3,5-tris(N-phenyl-2-benzylimidazole)benzene) (TPBI), TPBI also being suitable as electron-conducting material. In a further embodiment, it is possible to use compounds which comprise aromatic or heteroaromatic rings linked via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylbenzothiophene-S-oxides and disilylbenzothiophene-S,S-dioxides, as specified, for example, in PCT applications PCT/EP2008/058207 and PCT/EP2008/058106, which were yet to be published on the priority date of the present application, and disilyl compounds as disclosed in WO2008/034758, as a blocking layer for holes/excitons (4) or as matrix materials in the light-emitting layer (3).

In a preferred embodiment, the present invention relates to an OLED according to the invention comprising the layers (1) anode, (2) hole conductor layer, (3) light-emitting layer, (4) blocking layer for holes/excitons, (5) electron conductor layer and (6) cathode, and optionally further layers, wherein the hole-conducting layer contains at least one compound of formula (I).

Suitable electron conductor materials for the layer (5) of the OLEDs according to the invention comprise metals chelated with oxinoid compounds, such as 2,2',2"-(1,3,5-phenylene)tris[1-phenyl-1H-benzimidazole] (TPBI), tris(8-quinolinolato)aluminium (Alq3), compounds based on phenanthroline, such as 2,9-dimethyl-4,7-diphenyl-1,10-phenanthroline (DDPA=BCP) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), 8-hydroxyquinolinolatolithium (Liq), 4,7-diphenyl-1,10-phenanthroline (BPhen), bis(2-methyl-8-quinolinolato)-4-(phenyl-phenolato)aluminium (BAIq), 1,3-bis[2-(2,2'-bipyridin-6-yl)-1,3,4-oxadiazo-5-yl]benzene (Bpy-OXD), 6,6'-bis[5-(biphenyl-4-yl)-1,3,4-oxadiazol-2-yl]-2,2'-bipyridyl (BP-OXD-Bpy), 4-(naphthalen-1-yl)-3,5-diphenyl-4H-1,2,4-triazole (NTAZ), 2,9-bis(naphthalen-2-yl)-4,7-diphenyl-1,10-phenanthroline (NBphen), 2,7-bis[2-(2,2'-bipyridin-6-yl)-1,3,4-oxadiazo-5-yl]-9,9-dimethylfluorene (Bby-FOXD), 1,3-bis[2-(4-tert-butylphenyl)-1,3,4-oxadiazo-5-yl]benzene (OXD-7), tris(2,4,6-trimethyl-3-(pyridin-3-yl)phenyl)borane (3TPYMB), 1-methyl-2-(4-(naphthalen-2-yl)phenyl)-1H-imidazo[4,5-f][1,10]phenanthroline (2-NPIP), 2-phenyl-9,10-di(naphthalen-2-yl)anthracene (PADN), 2-(naphthalen-2-yl)-4,7-diphenyl-1,10-phenanthroline (HNBphen). The layer (5) may facilitate electron transport and may also be used as a buffer layer or as a barrier layer in order to prevent quenching of the exciton at the interfaces of the layers of the OLED. The layer (5) preferably improves the mobility of the electrons and reduces quenching of the exciton. In a preferred embodiment, TPBI is used as the electron conductor material.

Among the materials mentioned above as hole conductor materials and electron conductor materials, some may fulfil a number of functions. For example, some of the electron-conducting materials are simultaneously hole-blocking materials when they have a low-lying HOMO. These can be used, for example, in the blocking layer for holes/excitons (4). However, it is likewise possible that the function as a hole/exciton blocker is also carried out by the layer (5), such that the layer (4) can be omitted.

The electron conductor materials can also be doped. For example, the purpose of this doping is to improve the transport properties of the materials used, in order firstly to make the layer thicknesses more generous (avoidance of pinholes/short circuits) and in order secondly to minimise the operating voltage of the device. The electron conductor materials can be doped, for example, with alkali metals, for example Alq3 with lithium. In addition, electron conductors can be doped with salts such as Cs2CO3. Electronic doping is known to the person skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo. Appl. Phys. Lett., Vol. 82, No. 25, 23 Jun. 2003 and Pfeiffer et al., Organic Electronics 2003, 4, 89-103.

The cathode (6) is an electrode which serves to introduce electrons or negative charge carriers. Suitable materials for the cathode are selected from the group consisting of alkali metals of group Ia, for example Li, Cs, alkaline earth metals of group IIa, for example calcium, barium or magnesium, metals of group IIb of the Periodic Table of the Chemical Elements (old IUPAC version), comprising the lanthanides and actinides, for example samarium. In addition, it is also possible to use metals such as aluminium or indium, and combinations of all metals mentioned. In addition, lithium-containing organometallic compounds or LiF can be applied between the organic layer and the cathode in order to reduce the operating voltage.

The OLED according to the present invention may additionally comprise further layers which are known to the person skilled in the art. For example, a layer which facilitates the transport of the positive charge and/or matches the band gaps of the layers to one another may be applied between the layer (2) and the light-emitting layer (3). Alternatively, this further layer may serve as a protective layer. In an analogous manner, additional layers may be provided between the light-emitting layer (3) and the layer (4) in order to facilitate the transport of negative charge and/or to match the band gaps between the layers to one another. Alternatively, this layer may serve as a protective layer.

In a preferred embodiment, the OLED according to the invention, in addition to the layers (1) to (6), comprises at least one of the further layers mentioned below:

a hole injection layer between the anode (1) and the hole-transporting layer (2);

a blocking layer for electrons between the hole-transporting layer (2) and the light-emitting layer (3);

an electron injection layer between the electron-transporting layer (5) and the cathode (6).

Materials for a hole injection layer may be selected from copper phthalocyanine, 4,4',4"-tris(N-3-methylphenyl-N-phenylamino)triphenylamine (m-MTDATA), 4,4',4"-tris-(N-(2-naphthyl)-N-phenylamino)triphenylamine (2T-NATA), 4,4',4"-tris(N-(1-naphthyl)-N-phenylamino)triphenylamine (1T-NATA), 4,4',4"-tris(N,N-diphenylamino)triphenylamine (NATA), titanium oxide phthalocyanine, 2,3,5,6-tetrafluoro-7,7,8,8-tetracyanoquinodimethane (F4-TCNQ), pyrazino[2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxyphenyl)amino]-9,9-spirobifluorene (MeO-Spiro-TPD), 2,2'-bis[N,N-bis(4-methoxyphenyl) amino]-9,9-spirobifluorene (2,2'-IMO-Spiro-TPD), N,N'-diphenyl-N,N'-di-[4-(N,N-ditolylamino)phenyl]benzidine (NTNPB), N,N'-diphenyl-N,N'-di-[4-(N,N-diphenylamino) phenyl]benzidine (NTNPB), N,N'-di(naphthalen-2-yl)-N,N'-diphenylbenzene-1,4-diamine (β-NPP).

For example, LiF can be selected as a material for the electron injection layer.

The person skilled in the art is aware (for example on the basis of electrochemical studies) that suitable materials have to be selected. Suitable materials for the individual layers are known to the person skilled in the art and are disclosed, for example, in WO 00/70655.

In addition, it is possible that some of the layers used in the OLED according to the invention have been surface-treated in order to increase the efficiency of charge carrier transport. The selection of the materials for each of the layers mentioned is preferably determined in that an OLED with a high efficiency and service life is to be obtained.

The OLED according to the invention can be produced by methods known to the person skilled in the art. In general, the OLED according to the invention is produced by successive vapour deposition of the individual layers onto a suitable substrate. Suitable substrates are, for example, glass, inorganic semiconductors or polymer films. For vapour deposition, it is possible to use conventional techniques, such as thermal evaporation, chemical vapour deposition (CVD), physical vapour deposition (PVD) and others. In an alternative method, the organic layers of the OLED can be applied from solutions or dispersions in suitable solvents, wherein coating techniques known to the person skilled in the art are used.

In general, the different layers have the following thicknesses: anode (1) 50 to 500 nm, preferably 100 to 200 nm; hole-conducting layer (2) 5 to 100 nm, preferably 20 to 80 nm, light-emitting layer (3) 1 to 100 nm, preferably 10 to 80 nm, blocking layer for holes/excitons (4) 2 to 100 nm, preferably 5 to 50 nm, electron-conducting layer (5) 5 to 100 nm, preferably 20 to 80 nm, cathode (6) 20 to 1000 nm, preferably 30 to 500 nm. The relative position of the recombination zone of holes and electrons in the OLED according to the invention in relation to the cathode and hence the emission spectrum of the OLED can be influenced, inter alia, by the relative thickness of each layer. This means that the thickness of the electron transport layer should preferably be selected such that the position of the recombination zone is matched to the optical resonator property of the diode and hence to the emission wavelength of the emitter. The ratio of the layer thicknesses of the individual layers in the OLED depends on the materials used. The layer thicknesses of any additional layers used are known to the person skilled in the art.

Use of the quinone compounds of formula (I) in a conductor layer, specifically a hole conductor layer, makes it possible to obtain OLEDs with high efficiency and service life. The efficiency of the OLEDs can additionally be improved by optimising the other layers of the OLEDs. For example, high-efficiency cathodes such as Ca or Ba, optionally in combination with an intermediate layer of LiF, can be used. Shaped substrates and novel hole-transporting materials which bring about a reduction in the operating voltage or an increase in the quantum efficiency can likewise be used in the OLEDs according to the invention. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The present invention further relates to a hole-conducting layer containing at least one quinone derivative of formula (I), as defined above.

The OLEDs can be used in all devices in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in mobile telephones, laptops, digital cameras, vehicles and destination displays on buses and trains.

Furthermore, the quinone derivatives of formula (I) can be used in OLEDs with inverse structure. The structure of inverse OLEDs and the materials typically used therein are known to the person skilled in the art.

Furthermore, the present invention relates to a device selected from the group consisting of stationary visual display units such as visual display units of computers, televisions, visual display units in printers, kitchen appliances and advertising panels, illuminations, information panels, and mobile visual display units such as visual display units in mobile telephones, laptops, digital cameras, vehicles and destination displays on buses and trains, and illumination units comprising at least one organic light-emitting diode according to the invention or at least one hole-conducting layer according to the invention.

The quinone derivatives of general formula (I) are also particularly advantageously suitable as dopants for organic semiconductors. They generally serve as dopants for p-semiconductors.

Semiconductor materials which are doped with at least one quinine derivative of general formula (I) have a high charge transport mobility and/or have a high on/off ratio. They are particularly advantageously suitable for organic field-effect transistors (OFETs).

The compounds according to the invention and organic semiconductors doped therewith are advantageously suitable for the production of integrated circuits (ICs). For example, these include those circuits for which previously conventional MOSFETs (metal oxide semiconductor field-effect transistors (MOSFETs)) are used This is thus a CMOS-like semiconductor component, for example for microprocessors, microcontrollers, static RAM and other digital logic components.

In order to produce semiconductor materials, the compounds of formula (I) and the organic semiconductors doped therewith can be processed further in accordance with one of the following methods: printing (offset, flexographic, gravure, screen, inkjet, electrophotography), evaporation, laser transfer, photolithography and dropcasting. They are particularly suitable for a use in displays (specifically large and/or flexible displays) and RFID tags.

The object further relates to organic field-effect transistors comprising a substrate having at least a gate structure, a source electrode and a drain electrode and at least one compound of formula I, as defined above, as a dopant. The invention further relates to substrates having a large number of organic field-effect transistors, wherein at least some of the field-effect transistors contain at least one compound of formula I, as defined above, as a dopant.

The invention also relates to semiconductor components which comprise at least one such substrate.

A specific embodiment is a substrate having a pattern (topography) of organic field-effect transistors, wherein each transistor contains an organic semiconductor located on the substrate;
a gate structure for controlling the conductivity of the conductive channel; and
conductive source and drain electrodes at the two ends of the channel, wherein the organic semiconductor comprises at least one compound of formula (I). Furthermore, the organic field-effect transistor generally comprises a dielectric.

A further specific embodiment is a substrate having a pattern of organic field-effect transistors, wherein each transistor forms an integrated circuit or is part of an integrated circuit and wherein at least some of the transistors comprise at least one compound of formula (I).

In principle, suitable substrates are the materials known therefor. For example, suitable substrates include metals (preferably metals of groups 8, 9, 10 or 11 of the Periodic Table, such as Au, Ag, Cu), oxide materials (such as glass, quartz, ceramics, $SiO_2$), semiconductors (for example doped Si, doped Ge), metal alloys (for example based on Au, Ag, Cu, etc.), semiconductor alloys, polymers (for example polyvinylchloride, polyolefins such as polyethylene and polypropylene, polyesters, fluoropolymers, polyamides, polyimides, polyurethanes, polyalkyl(meth)acrylates, polystyrene and mixtures and composites thereof), inorganic solids (for example ammonium chloride), paper and combinations thereof. The substrates may be flexibly or inflexibly solid, with curved or planar geometries, irrespective of the desired application.

A typical substrate for semiconductor components comprises a matrix (for example a quartz or polymer matrix) and, optionally, a dielectric cover layer.

Suitable dielectrics are $SiO_2$, polystyrene, poly-α-methylstyrene, polyolefins (such as polypropylene, polyethylene, polyisobutene), polyvinylcarbazole, fluorinated polymers (for example Cytop, CYMM), cyanopullanes, polyvinylphenol, poly-p-xylene, polyvinylchloride, or polymers crosslinkable thermally or by atmospheric moisture. Specific dielectrics are "self assembled nanodielectrics", that is to say polymers which are obtained from monomers containing SiCl functionalities, such as $Cl_3SiOSiCl_3$, $Cl_3Si-(CH_2)_6-SiCl_3$, $Cl_3Si-(CH_2)_{12}-SiCl_3$ and/or which are crosslinked by atmospheric moisture or by the addition of water diluted with solvents (for example see Faccietti Adv. Mat. 2005, 17, 1705-1725). Instead of water, it is also possible for hydroxyl-group-containing polymers such as polyvinylphenol or polyvinyl alcohol or copolymers of vinylphenol and styrene to serve as crosslinking components. It is also possible for at least one further polymer to be present during the crosslinking process, for example polystyrene, which is then also crosslinked (see Facietti, US patent application 2006/0202195).

The substrate may additionally have electrodes, such as gate, drain and source electrodes of OFETs, which are normally localized on the substrate (for example deposited onto or embedded into a non-conductive layer on the dielectric). The substrate may additionally comprise conductive gate electrodes of the OFETs, which are typically arranged below the dielectric cover layer (that is to say the gate dielectric).

In accordance with a specific embodiment, an insulator layer (gate insulating layer) is present on at least part of the substrate surface. The insulator layer comprises at least one insulator which is preferably selected from inorganic insulators such as $SiO_2$, SiN, etc., ferroelectric insulators such as $Al_2O_3$, $Ta_2O_5$, $La_2O_5$, $TiO_2$, $Y_2O_3$, etc., organic insulators such as polyimides, benzocyclobutene (BCB), polyvinyl alcohols, polyacrylates, etc., and combinations thereof.

Suitable materials for source and drain electrodes are in principle electrically conductive materials. These include metals, preferably metals of groups 8, 9, 10 or 11 of the Periodic Table, such as Pd, Au, Ag, Cu, Al, Ni, Cr, etc. Also suitable are conductive polymers such as PEDOT (=poly(3, 4-ethylenedioxythiophene)):PSS (=poly(styrenesulphonate)), polyaniline, surface-modified gold, etc. Preferred electrically conductive materials have a specific resistance of less than $10^{-3}$ ohm×metre, preferably less than $10^{-4}$ ohm× metre, in particular less than $10^{-6}$ or $10^{-7}$ ohm×metre.

In a specific embodiment, drain and source electrodes are present at least in part on the organic semiconductor material. Of course, the substrate may comprise further components as used conventionally in semiconductor materials or ICs, such as insulators, resistors, capacitors, strip conductors, etc.

The electrodes may be applied by conventional methods, such as evaporation, lithographic methods or another structuring process.

The semiconductor materials may also be processed using suitable auxiliaries (polymers, surfactants) in disperse phase by printing.

In a preferred embodiment, the deposition of at least one compound of general formula (I) (and optionally at least one organic semiconductor material) is carried out by a gas phase deposition method (physical vapour deposition, PVD). PVD processes are performed under high-vacuum conditions and comprise the following steps: evaporation, transport, deposition. It has surprisingly been found that the compounds of general formula (I) are particularly advantageously suitable for use in a PVD process, since they essentially do not decompose and/or form undesired by-products. The material deposited is obtained in high purity. In general, for PVD, at least one compound of general formula (I), optionally in combination with at least one organic semiconductor, is heated to a temperature above its evaporation temperature and is deposited on a substrate by cooling below the crystallisation temperature. The temperature of the substrate in the deposition is preferably in a range of approximately 20 to 250° C., more preferably from 50 to 200° C.

The resulting semiconductor layers generally have a thickness which is sufficient for ohmic contact between source and drain electrodes. The deposition can be carried out under an inert atmosphere, for example, under nitrogen, argon or helium.

The deposition is typically effected at ambient pressure or at reduced pressure. A suitable pressure range is from approximately 10-7 to 1.5 bar.

The layer containing at least one compound of formula (I) is preferably deposited on the substrate in a thickness from 10 to 1000 nm, more preferably from 15 to 250 nm.

The compounds of general formula (I) may also advantageously be processed from solution. For example, at least one compound of general formula (I) (and optionally at least one semiconductor material) is applied to a substrate by spin coating. The compounds of formula (I) are also suitable for the production of semiconductor elements, specifically OFETs, by a printing process. It is possible for this purpose to use conventional printing processes (inkjet, flexographic, offset, gravure; intaglio printing, nanoprinting). Preferred solvents for the use of compounds of formula (I) in a printing process are aromatic solvents such as toluene, xylene, etc. It is also possible to add thickening substances such as polymers, for example polystyrene, etc., to these "semiconductor inks". In this case, the aforementioned compounds are used as a dielectric.

In a specific embodiment the field-effect transistor according to the invention is a thin-film transistor (TFT). In accordance with a conventional structure, a thin-film transistor has a gate electrode disposed on the substrate, a gate insulation layer disposed thereon and on the substrate, a semiconductor layer disposed on the gate insulator layer, an ohmic contact layer on the semiconductor layer, and a source electrode and a drain electrode on the ohmic contact layer.

In a suitable embodiment, the surface of the substrate, before the deposition of at least one compound of general formula (I) (and optionally of at least one organic semiconductor material), is subjected to a modification. This modification serves to form regions which bind the dopants and/or semiconductor materials and/or regions on which no dopants and/or semiconductor materials can be deposited. The surface of the substrate is preferably modified with at least one compound (C1) which is suitable for binding to the surface of the substrate and to the compounds of formula (I). In a suitable embodiment some of the surface or the complete surface of the substrate is coated with at least one compound (C1) in order to enable improved deposition of at least one compound of general formula (I) (and optionally further semiconductive compounds). A further embodiment comprises the deposition of a pattern of compounds of general formula (C1) on the substrate by a corresponding production process. These include the mask processes known for this purpose and "patterning" processes, as described for example in US-2007-0190783-A1, which is incorporated here fully by reference.

Suitable compounds of formula (C1) are capable of a binding interaction both with the substrate and with at least one dopant compound of general formula (I) and/or at least one semiconductor compound. The term "binding interaction" includes the formation of a chemical bond (covalent bond), ionic bond, coordinative interaction, Van der Waals interactions, for example dipole-dipole interactions etc.), and combinations thereof. Suitable compounds of general formula (C1) are:

silanes, phosphonic acids, carboxylic acids, hydroxamic acids such as alkyltrichlorosilanes, for example n-octadecyltrichlorosilane; compounds with trialkoxysilane groups, for example alkyltrialkoxysilanes such as n-octadecyltrimethoxysilane, n-octadecyltriethoxysilane, n-octadecyltri(n-propyl)oxysilane, n-octadecyltri(isopropyl)oxysilane; trialkoxyaminoalkylsilanes such as triethoxyaminopropylsilane and N[(3-triethoxysilyl)propyl]ethylenediamine; trialkoxyalkyl-3-glycidyl ether silanes such as triethoxypropyl-3-glycidyl ether silane; trialkoxyallylsilanes such as allyltrimethoxysilane; trialkoxy(isocyanatoalkyl)silanes; trialkoxysilyl(meth)acryloxyalkanes and trialkoxysilyl(meth)acrylamidoalkanes such as 1-triethoxysilyl-3-acryloxypropane.

amines, phosphines and sulphur-containing compounds, especially thiols.

The compound (C1) is preferably selected from alkyltrialkoxysilanes, specifically n-octadecyltrimethoxysilane, n-octadecyltriethoxysilane; hexaalkyldisilazanes, and especially hexamethyldisilazane (HMDS); C8-C30 alkylthiols, especially hexadecanethiol; mercaptocarboxylic acids and mercaptosulphonic acids, especially mercaptoacetic acid, 3-mercaptopropionic acid, mercaptosuccinic acid, 3-mercapto-1-propanesulphonic acid and the alkali metal and ammonium salts thereof.

Various semiconductor architectures comprising the semiconductors according to the invention are also conceivable, for example top contact, top gate, bottom contact, bottom gate, or else a vertical construction, for example a VOFET (vertical organic field-effect transistor), as described for example in US 2004/0046182.

The layer thicknesses are, for example, 10 nm to 5 µm in semiconductors, 50 nm to 10 µm in the dielectric, and the electrodes may, for example, be 20 nm to 1 µm thick. The OFETs may also be combined to form other components such as ring oscillators or inverters.

A further aspect of the invention is the provision of electronic components which comprise a plurality of semiconductor components, which may be n- and/or p-semiconductors. Examples of such components are field-effect transistors (FETs), bipolar junction transistors (BJTs), tunnel diodes, converters, light-emitting components, biological and chemical detectors or sensors, temperature-dependent detectors, photodetectors such as polarization-sensitive photodetectors, gates, AND, NAND, NOT, OR, TOR and NOR gates, registers, switches, timer units, static or dynamic stores and other dynamic or sequential, logical or other digital components including programmable circuits.

A specific semiconductor element is an inverter. In digital logic, the inverter is a gate which inverts an input signal. The inverter is also referred to as a NOT gate. Real inverter circuits have an output current which constitutes the opposite of the input current. Typical values are, for example, (0, +5V) for TTL circuits. The performance of a digital inverter reproduces the voltage transfer curve (VTC), that is to say the plot of input current against output current. Ideally, it is a staged function and, the closer the real measured curve approximates to such a stage, the better the inverter is. In a specific embodiment of the invention, the compounds of formula (I) are used as dopants for organic semiconductors in an inverter.

The quinone derivatives according to the invention of general formula (I) are also particularly advantageously suitable for use in organic photovoltaics (OPVs).

In organic solar cells free charge carriers are not produced directly by the light, but instead excitons, that is to say electrically neutral excitation states in the form of electron-hole pairs are first formed. These excitons can be separated at suitable interfaces (photoactive interfaces). In principle, organic donor-acceptor interfaces or interfaces with an inorganic semiconductor are suitable for exciton separation. For this, it is necessary for excitons which are generated in the bulk of the organic material to be able to diffuse at these photoactive interfaces.

Organic solar cells are generally layered in structure and generally comprise at least the following layers: anode, photoactive layer and cathode. These layers generally consist of a substrate conventional therefor. The photoactive layer generally contains at least one electron donor material and at least one electron acceptor material, thus enabling a donor-acceptor junction. This junction may be designed in the form of a "flat-hetero-junction" or preferably a "bulk-hetero-junction". Organic solar cells with photoactive donor-acceptor junctions in the form of a bulk-hetero-junction are based on reducing the mean distance to the next interface. For this purpose, the mixed layers of donors and acceptors can be used which form a interpenetrating network in which internal donor-acceptor-hetero-junctions are possible.

In addition to the photoactive layer, one or more further layers may also be provided. For example these include
layers with electron conducting properties (ETL, electron transport layer),
layers which contain a hole-conducting material (hole transport layer, HTL) which must not absorb,
exciton- and hole-blocking layers (for example exciton blocking layers, EBL), which should not absorb, and
multiplication layers.

The organic solar cells according to the invention contain at least one quinone derivative of general formula (I). This is preferably used as a dopant for a charge transport material in the photoactive layer and/or at least one further layer which contains an organic semiconductor material. In particular, the organic solar cells according to the invention contain at least one quinone derivative of general formula (I) as a p-dopant in the photoactive layer and/or a hole-conducting layer.

Suitable substrates for organic solar cells are, for example, oxide materials (such as glass, ceramic, SiO2, in particular quartz, etc.), polymers (for example polyvinyl chloride, polyolefins such as polyethylene and polypropylene, polyesters, fluoropolymers, polyamides, polyurethanes, polyalkyl (meth)acrylates, polystyrene and mixtures and composites thereof) and combinations thereof.

Suitable electrodes (cathode, anode) are in principle metals (preferably of groups 8, 9, 10 or 11 of the Periodic Table, for example Pt, Au, Ag, Cu, Al, In, Mg, Ca), semiconductors (for example doped Si, doped Ge, indium tin oxide (ITO), gallium indium tin oxide (GITO), zinc indium tin oxide (ZITO), etc.), metal alloys (for example based on Pt, Au, Ag, Cu, etc., especially Mg/Ag alloys), semiconductor alloys, etc.

The material used for the electrode facing the light (the anode in a normal structure, the cathode in an inverse structure) is preferably a material which is transparent at least in part to the incident light. This specifically includes glass and transparent polymers, such as polyethylene terephthalate. The electrical contact connection is generally effected by means of metal layers and/or transparent conductive oxides (TCOs). These preferably include ITO, FTO, ZnO, TiO2, Ag, Au, Pt.

The layer facing the light is designed such that it is sufficiently thin to bring about only minimal light absorption but is thick enough to enable good charge transport of the extracted charge carriers. The thickness of the layer is preferably in a range of 20 to 200 nm.

In a specific embodiment, the material used for the electrode facing away from the light (the cathode in a normal structure, the anode in an inverse structure) is a material which reflects, at least in part, the incident light. This includes metal films, preferably of Ag, Au, Al, Ca, Mg, In and mixtures thereof. The thickness of the layer is preferably in a range of 50 to 300 nm.

Suitable exciton- and hole-blocking layers are described for example in U.S. Pat. No. 6,451,415. For example, suitable materials for exciton blocker layers are 2,9-dimethyl-4,7-diphenyl-1,10-phenanthroline (BCP), 4,7-diphenyl-1,10-phenanthroline (Bphen), 1,3-bis[2-(2,2'bipyridin-6-yl)-1,3,4-oxadiazo-5-yl]benzene (BPY-OXD), polyethylene dioxythiophene (PEDOT), etc. A material which is simultaneously well suited for electron transport is preferably used. BCP, Bphen and BPY-OXD are preferred.

If provided, the thickness of the layers having exciton-blocking properties is preferably in a range of 1 to 50 nm, more preferably 2 to 20 nm.

The solar cells according to the invention are preferably based on photoactive donor-acceptor heterojunctions. HTM (hole transport material) and the corresponding ETM (exciton transport material) are selected in such a way that a rapid electron transfer takes place on the ETM after excitation of the compounds. The heterojunction may be flat (smooth) (see Two layer organic photovoltaic cell, C. W. Tang, Appl. Phys. Lett., 48 (2), 183-185 (1986) or N. Karl, A. Bauer, J. Holzapfel, J. Marktanner, M. Möbus, F. Stölzle, Mol. Cryst. Liq. Cryst., 252, 243-258 (1994).). The heterojunction may also be designed as a bulk heterojunction (interpenetrating donor-acceptor network) (for example see C. J. Brabec, N. S. Sariciftci, J. C. Hummelen in Adv. Funct. Mater., 11(1), 15 (2001)).

In a suitable embodiment, the photoactive donor-acceptor junctions are produced by a gas phase deposition process (physical vapour deposition, PVD). Suitable processes are described for example in US 2005/0227406, to which reference is made here. To this end, the semiconductor materials for the photoactive layer may be subjected to a gas phase deposition. The semiconductor material and dopant (specifically p-semiconductor material and at least one quinone derivative of formula (I)) may also be subjected to a common gas phase separation within the meaning of a cosublimation. Furthermore, photoactive layers with a bulk-hetero-junction can be produced by cosublimation of at least one donor material, at least one acceptor material and optionally at least one dopant. PVD processes are performed under high-vacuum conditions and comprise the following steps: evaporation, transport, deposition. The deposition is preferably carried out at a pressure in the range of approximately 10-5 mbar to 10-7 mbar. The deposition rate is preferably in a range of approximately 0.01 to 10 nm/s. The temperature of the substrate during the deposition process is preferably in a range of approximately −100 to 300° C., more preferably of −50 to 250° C. The deposition may take place in an inert atmosphere, for example under nitrogen, argon or lithium.

The other layers forming the solar cell can be produced by conventional methods known to the person skilled in the art. These include vapour deposition under vacuum or in an inert gas atmosphere, laser ablation, or solution or dispersion processing methods such as spin coating, knife coating, casting methods, spray application, dip coating or printing (for example inkjet, flexographic, offset, gravure; intaglio printing, nanoimprinting).

The solar cells according to the invention may be provided in the form of individual cells of normal structure. In a specific embodiment, one such cell comprises the following layer structure:

an at least partially light-permeable substrate,
a first electrode (front electrode, anode),
a hole-conducting layer,
a photoactive layer,
electron-conducting layer,
an exciton-blocking/electron-conducting layer,
a second electrode (rear electrode, cathode).

The solar cells according to the invention may also be provided in the form of individual cells of inverse structure. In a specific embodiment such a cell comprises the following layer structure:
an at least partially light-permeable substrate,
a first electrode (front electrode, cathode),
an exciton-blocking/electron-conducting layer,
electron-conducting layer,
a photoactive layer,
a hole-conducting layer,
a second electrode (rear electrode, anode).

The compounds of formula (I) can be used in solar cells with MiM, pin, pn, Mip or Min structure (M=metal, p=p-doped organic or inorganic semiconductor, n=n-doped organic or inorganic semiconductor, i=intrinsically conductive system of organic layers; for example see J. Drechsel et al., Org. Electron., 5 (4), 175 (2004) or Maennig et al., Appl. Phys. A 79, 1-14 (2004)).

The compounds of formula (I) can also be used in tandem cells, as described by P. Peumans, A. Yakimov, S. R. Forrest in J. Appl. Phys, 93 (7), 3693-3723 (2003) (see also U.S. Pat. No. 4,461,922, U.S. Pat. No. 6,198,091 and U.S. Pat. No. 6,198,092).

The compounds of formula (I) can also be used in tandem cells which are constructed from two or more stacked MiM, pin, Mip or Min diodes (see patent application DE 103 13 232.5 and J. Drechsel et al., Thin Solid Films, 451452, 515-517 (2004)).

The layer thicknesses of the M, n, i and p layers are typically 10 to 1000 nm, preferably 10 to 400 nm, more preferably 10 to 100 nm.

Suitable semiconductor materials for the organic solar cells are those mentioned above, to which reference is made herein.

The invention will now be described in greater detail on the basis of the following, non-limiting examples.

EXAMPLES

I) Production of Quinone Derivatives

Example 1

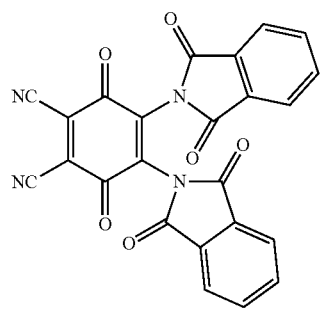

(I.A)

33.4 g (147 mMol) of 2,3-dichloro-5,6-dicyano benzoquinone (DDQ) were dissolved in 500 ml acetonitrile and mixed with 54.5 g (294 mMol) of phthalimide potassium salt. The mixture was heated to reflux and stirred for 12 hours, wherein a dark brown suspension was obtained. After cooling, the precipitate was suctioned off, the residue was suspended in 500 ml of water and stirred for 1 hour at 90° C. The residue was suctioned off hot and washed with approximately 1000 ml of hot water in a number of portions. It was then washed once with a little ethanol and the product was dried in a vacuum drying cupboard at 100° C. 9.3 g of a yellow solid were obtained.

Thermostability: >400° C.
Sublimation temperature: 240° C.

II) Application-Specific Properties

Example 2

Diffusion (migration) measurements of the compound (I.A) and of F6TNAP compared to UPS

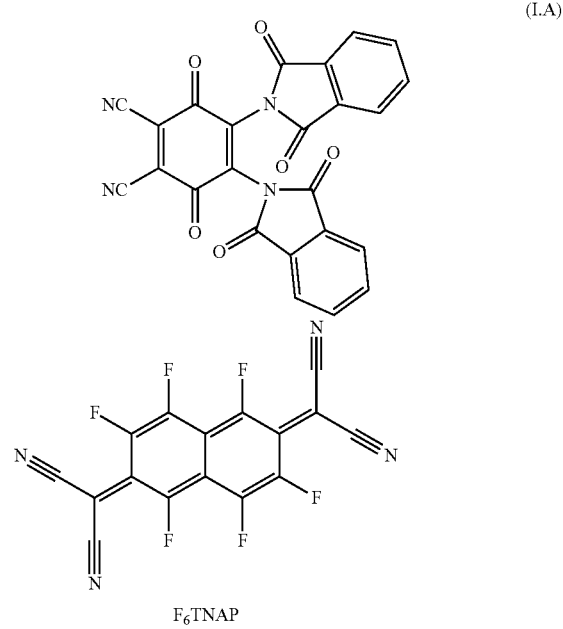

The following samples were used for the diffusion measurements. In each case an Si wafer coated with a 50 nm silver layer was used as a substrate.

Comparison:
1) 10 nm of pure NPD (N,N'-bis-1-(naphthyl)-N,N'-diphenyl-1,1'-biphenyl-4,4'-diamine)
2) 10 nm of NPD, doped with 2% by weight F6TNAP
3) 30 nm of pure NPD subjected to vapour deposition on a layer of 10 nm NPD, doped with 2% by weight F6TNAP The results are reproduced in FIG. 1.

Any migration of the dopant into the adjacent undoped layer can be determined directly by means of UPS. It is known from XPS measurements that the comparative dopant F6TNAP tends towards diffusion. This could be confirmed by the UPS measurements on the three above-mentioned substrates.

The HOMO of the pure 10 nm NPD layer (1) has an energy difference of 1.3 eV to the Fermi level. Owing to the doping, the HOMO of the substrate (2) (10 nm NPD, doped with 2% by weight F6TNAP) only has an energy difference of 0.6 eV. Without a migration of dopant into the upper NPD layer, the substrate (3) should have the same HOMO as substrate (1). However, the measured energy difference between the HOMO and Fermi levels is 0.9 eV and is thus 0.4 eV less than the difference between the Fermi level and pure NPD. This reveals a significant diffusion of F6TNAP into the 30 nm NPD layer.

In accordance with the invention:
1) 10 nm pure NPD
2) 10 nm NPD, doped with 2% by weight quinone derivative (I.A)
3) 30 nm pure NPD subjected to vapour deposition on a layer of 10 nm NPD, doped with 2% by weight quinone derivative (I.A)

Figure 2:
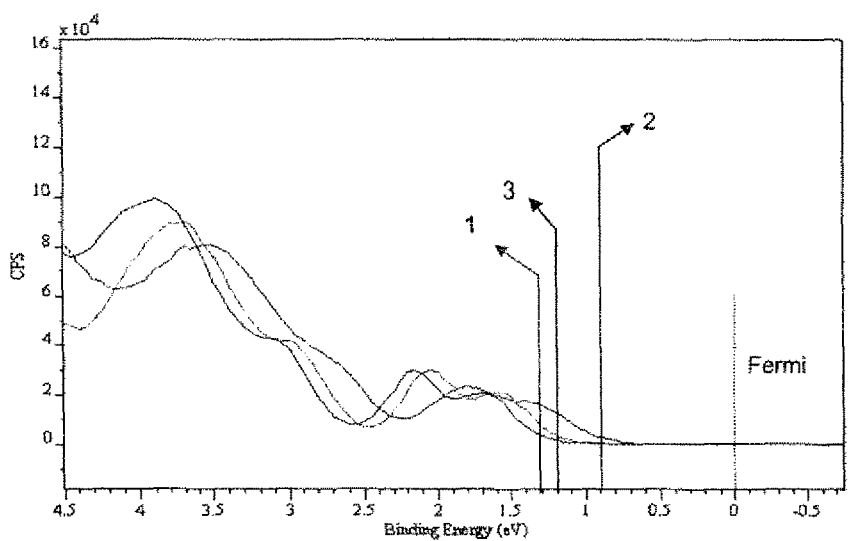
FIG. 2 depicts the diffusion measurement of the compound I.A. compared to UPS.

The results are reproduced in FIG. 2.

The measured energy difference between the HOMO of the substrate (3) and the Fermi level is only 0.1 eV less than the difference between the Fermi level and pure NPD. This reveals that the quinone derivative according to the invention (IA) exhibits no significant diffusion into the 30 nm NPD layer.

TABLE 1

Comparison with commercial dopants

| Dopant | F4-TCNQ | MoO₃ | (I.A) |
|---|---|---|---|
| Mw. | 276.15 | — | 448.35 |
| IP | 7.82 eV | — | 7.45 eV |
| EA | 4.96 eV | — | 4.82 eV |
| Evaporation temperature under high vacuum ($10^{-7}$ mbar) | less than 80° C. | 470 ± 10° C. (slightly contaminatable) | 190 ± 10° C. |

Mw. = molecular weight
EA = electron affinity
IP = ionisation potential

The sublimation temperature of F4-TCNQ is too low, whilst that of MoO3 is too high. Both are only suited for use in OLEDs to a limited extent.

The invention claimed is:

1. A quinone derivative of general formula (I)

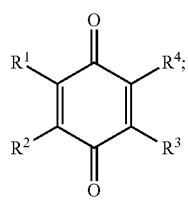

(I)

wherein 1, 2 or 3 of the radicals $R^1$ to $R^4$ are CN,
wherein 1, 2, or 3 of the radicals $R^1$ to $R^4$, independently of one another, are phthalimide radical of general formula (II)

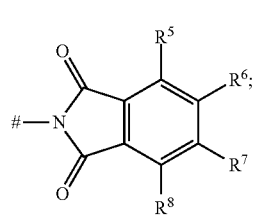

(II)

wherein # is the linking point to a ring carbon atom of the quinone ring, wherein $R^5$, $R^6$, $R^7$, and $R^8$, independently of one another, are selected from hydrogen, fluorine, chlorine, bromine, cyano, nitro, nitroso, formyl, acyl, COOH, carboxylate, alkylcarbonyloxy, carbamoyl, SO₃H, sulphonate, sulphamino, sulphamide, amidino, $NE^1E^2$, alkyl, alkoxy, alkylamino, alkylthio, alkylsulphinyl, alkylksulphonyl, alkenyl, alkadienyl, alkynyl, cycloalkyl, bicycloalkyl, cycloalkenyl, heterocycloalkyl, aryl, heteroaryl, or a condensed ring system containing 1, 2, or 3 further rings comprising two or more adjacent radicals selected from $R^5$ to $R^8$ together with the carbon atom of the benzene nucleus to which $R^5$ to $R^8$ are bound, wherein the alkyl, alkoxy, alkylamino, alkylthio, alkylsulphinyl, alkylksulphonyl, alkenyl, alkadienyl, alkynyl, cycloalkyl, bicycloalkyl, cycloalkenyl, heterocycloalkyl, aryl, and heteroaryl groups may be unsubstituted or substituted, and wherein $E^1$ and $E^2$, independently of one another, are selected from hydrogen, alkyl, cycloalkyl, or aryl, and wherein the radicals $R^1$ to $R^4$, which are not selected from CN or a phthalimide radical of general formula (II), are selected independently of one another from hydrogen, fluorine, chlorine, bromine, cyano, nitro, nitroso, formyl, acyl, COOH, carboxylate, alkylcarbonyloxy, carbamoyl, SO₃H, sulphonate, sulphamino, sulphamide, amidino, $NE^3E^4$, alkyl, alkoxy, alkylamino, alkylthio, alkylsulphinyl, alkylsulphonyl, alkenyl, alkadienyl, alkynyl, cycloalkyl, bicycloalkyl, cycloalkenyl, heterocycloalkyl, aryl, heteroaryl, or a condensed ring system containing 1, 2, or 3 further rings comprising $R^1$ and $R^2$ and/or $R^3$ and $R^4$ together with the carbon atom of the quinone ring to which $R^1$ and $R^2$ and/or $R^3$ and $R^4$ are bound, wherein $E^3$ and $E^4$, independently of one another, are selected from hydrogen, alkyl, cycloalkyl or aryl, and wherein the alkyl, alkoxy, alkylamino, alkylthio, alkylsulphinyl, alkylksulphonyl, alkenyl, alkadienyl, cycloalkyl, bicycloalkyl, cycloalkenyl, heterocycloalkyl, aryl, or heteroaryl may be unsubstituted or substituted.

2. The quinone derivative according to claim 1, wherein none of the radicals $R^1$ to $R^4$ is selected from fluorine, chlorine, or bromine.

3. The quinone derivative according to claim 1, wherein two of the radicals $R^1$ to $R^4$ are cyano.

4. The quinone derivative according to claim 1, wherein two of the radicals $R^1$ to $R^4$ are a phthalimide radical of general formula (II).

5. The quinone derivative according to claim 1, wherein none of the radicals $R^5$ to $R^8$ is selected from fluorine, chlorine, or bromine.

6. A quinone derivative of general formula (I) having the following structure:

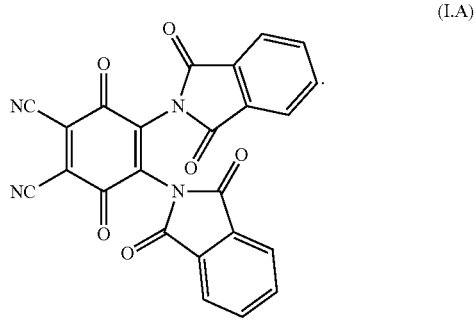

(I.A)

7. A method for producing quinone derivatives of general formula (I) comprising:

reacting a compound of formula (I), in which at least one of the radicals $R^1$ to $R^4$ is Cl or Br, with a phthalimide compound of general formula (II.a)

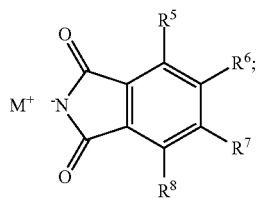

(II.a)

wherein $M^+$ is a cation equivalent, wherein $R^5$, $R^6$, $R^7$, and $R^8$, independently of one another, are selected from hydrogen, fluorine, chlorine, bromine, cyano, nitro, nitroso, formyl, acyl, COOH, carboxylate, alkylcarbonyloxy, carbamoyl, SO$_3$H, sulphonate, sulphamino, sulphamide, amidino, NE$^1$E$^2$, alkyl, alkoxy, alkylamino, alkylthio, alkylsulphinyl, alkylksulphonyl, alkenyl, alkadienyl, alkynyl, cycloalkyl, bicycloalkyl, cycloalkenyl, heterocycloalkyl, aryl, heteroaryl, or a condensed ring system containing 1, 2, or 3 further rings comprising two or more adjacent radicals selected from $R^5$ to $R^8$ together with the carbon atom of the benzene nucleus to which $R^5$ to $R^8$ are bound, wherein the alkyl, alkoxy, alkylamino, alkylthio, alkylsulphinyl, alkylksulphonyl, alkenyl, alkadienyl, alkynyl, cycloalkyl, bicycloalkyl, cycloalkenyl, heterocycloalkyl, aryl, and heteroaryl groups may be unsubstituted or substituted, and wherein $E^1$ and $E^2$, independently of one another, are selected from hydrogen, alkyl, cycloalkyl, or aryl;

and wherein the compound of formula (I) has the following structure—

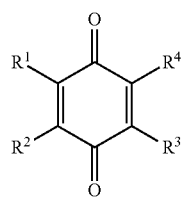

(I)

wherein 1, 2 or 3 of the radicals $R^1$ to $R^4$ are CN, wherein 1, 2, or 3 of the radicals $R^1$ to $R^4$, independently of one another, are a phthalimide radical of general formula (II)

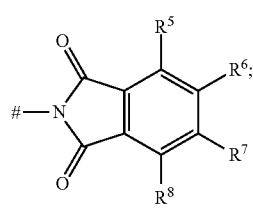

(II)

wherein # is the linking point to a ring carbon atom of the quinone ring, wherein $R^5$, $R^6$, $R^7$, and $R^8$ are defined as above, and wherein the radicals $R^1$ to $R^4$, where provided, which are not selected from CN or a phthalimide radical of general formula (II), are selected independently of one another from hydrogen, fluorine, chlorine, bromine cyano nitro, nitroso, formyl, acyl, COOH, carboxylate, alkylcarbonyloxy, carbamoyl, SO$_3$H, sulphonate, sulphamino, sulphamide, amidino, NE$^3$E$^4$, alkyl, alkoxy, alkylamino, alkylthio, alkylsulphinyl, alkylksulphonyl, alkenyl, alkadienyl, alkynyl, cycloalkyl, bicycloalkyl, cycloalkenyl, heterocycloalkyl, aryl, heteroaryl, or a condensed ring system containing 1, 2, or 3 further rings comprising $R^1$ and $R^2$ and/or $R^3$ and $R^4$ together with the carbon atom of the quinone ring to which $R^1$ and $R^2$ and/or $R^3$ and $R^4$ are bound, wherein $E^3$ and $E^4$, independently of one another, are selected from hydrogen, alkyl, cycloalkyl or aryl, and wherein the alkyl, alkoxy, alkylamino, alkylthio, alkylsulphinyl, alkylksulphonyl, alkenyl, alkadienyl, alkynyl, cycloalkyl, bicycloalkyl, cycloalkenyl, heterocycloalkyl, aryl, or heteroaryl may be unsubstituted or substituted.

8. An organic electronic device comprising a quinone derivative of general formula (I),

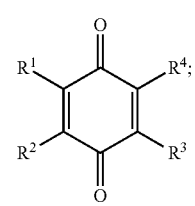

(I)

wherein 1, 2 or 3 of the radicals $R^1$ to $R^4$ are CN, wherein 1, 2, or 3 of the radicals $R^1$ to independently of one another, are a phthalimide radical of general formula (II)

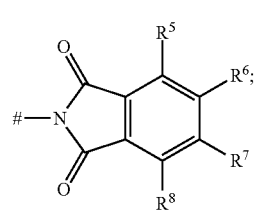

(II)

wherein # is the linking point to a ring carbon atom of the quinone ring, wherein $R^5$, $R^6$, $R^7$, and $R^8$, independently of one another, are selected from hydrogen, fluorine, chlorine, bromine, cyano, nitro, nitroso, formyl, acyl, COOH, carboxylate, alkylcarbonyloxy, carbamoyl, SO$_3$H, sulphonate, sulphamino, sulphamide, amidino, NE$^1$E$^2$, alkyl, alkoxy, alkylamino, alkylthio, alkylsulphinyl, alkylksulphonyl, alkenyl, alkadienyl, alkynyl, cycloalkyl, bicycloalkyl, cycloalkenyl, heterocycloalkyl, aryl, heteroaryl, or a condensed ring system containing 1, 2, or 3 further rings comprising two or more adjacent radicals selected from $R^5$ to $R^8$ together with the carbon atom of the benzene nucleus to which $R^5$ to $R^8$ are bound, wherein the alkyl, alkoxy, alkylamino, alkylthio, alkylsulphinyl, alkylksulphonyl, alkenyl, alkadienyl, alkynyl, cycloalkyl, bicycloalkyl, cycloalkenyl, heterocycloalkyl, aryl, and heteroaryl groups may be unsubstituted or substituted, and wherein $E^1$ and $E^2$, independently of one another, are selected from hydrogen, alkyl, cycloalkyl, or aryl, and wherein the radicals $R^1$ to $R^4$, where provided, which are not selected from CN or a phthalimide radical of general formula (II), are selected independently of one another from hydrogen, fluorine, chlorine, bromine, cyano, nitro, nitroso, formyl, acyl, COOH, carboxylate, alkylcarbonyloxy, carbamoyl, $SO_3H$, sulphonate, sulphamino, sulphamide, amidino, $NE^3E^4$, alkyl, alkoxy, alkylamino, alkylthio, alkylsulphinyl, alkylksulphonyl, alkenyl, alkadienyl, alkenyl, cycloalkyl, bicycloalkyl, cycloalkenyl, heterocycloalkyl, aryl, -heteroaryl, or a condensed ring system containing 1, 2, or 3 further rings comprising $R^1$ and $R^2$ and/or $R^3$ and $R^4$ together with the carbon atom of the quinone ring to which $R^1$ and $R^2$ and/or $R^3$ and $R^4$ are bound, wherein $E^3$ and $E^4$, independently of one another, are selected from hydrogen, alkyl, cycloalkyl or aryl, and wherein the alkyl, alkoxy, alkylamino, alkylthio, alkylsulphinyl, alkylksulphonyl, alkenyl, alkadienyl, alkenyl, cycloalkyl, bicycloalkyl, cycloalkenyl, heterocycloalkyl, aryl, or heteroaryl may be unsubstituted or substituted.

9. The device according to claim 8, comprising a dopant for organic semiconductive materials, wherein the dopant comprises the quinone derivative.

10. The device according to claim 8, wherein the device comprises an organic light-emitting diode.

11. The device according to claim 10, comprising a conductor layer or a hole conductor layer, wherein the conductor layer or the hole conductor layer comprises the quinone derivative.

12. The device according to claim 8, comprising a hole-conducting layer, wherein the hole-conducting layer comprises the quinone derivative.

13. The device according to claim 8, wherein the device is selected from the group consisting of stationary visual display units; illuminations; information panels; and mobile visual display units.

14. The device according to claim 13, wherein the stationary visual display units are selected from visual display units of computers, televisions, printers, kitchen appliances, or advertising panels.

15. The device according to claim 13, wherein the mobile display units are selected from visual display units in mobile telephones, laptops, digital cameras, vehicles, or destination displays on buses or trains.

16. The device according to claim 8, wherein the device is an organic field-effect transistor.

17. The device according to claim 16, wherein the organic field-effect transistor comprises a substrate having at least a gate structure, a source electrode, a drain electrode, and a dopant, wherein the dopant comprises the quinone derivative.

18. The device according to claim 8, wherein the device is an organic photovoltaic comprising a dopant, wherein the dopant comprises the quinone derivative.

19. The device according to claim 18, wherein the dopant comprises a dopant for a charge transport material.

20. The device according to claim 8, wherein the device comprises a substrate comprising a large number of organic field-effect transistors, wherein at least one of the field-effect transistors comprises the quionone derivative.

21. The device according to claim 8, wherein the device comprises a semiconductor component comprising at least one substrate comprising a large number of organic field-effect transistors, wherein at least one of the field-effect transistors comprises the quionone derivative.

22. The device according to claim 8, wherein the device is an organic solar cell.

* * * * *